US012778957B2

(12) United States Patent
Ravindran et al.

(10) Patent No.: US 12,778,957 B2
(45) Date of Patent: Nov. 3, 2026

(54) COMPOSITION FOR ENHANCING INTRA-CELLULAR NITRIC OXIDE GENERATION

(71) Applicants: INSTITUTE OF LIFE SCIENCES, Bhubaneswar (IN); TRANSLATIONAL HEALTH SCIENCES AND TECHNOLOGY INSTITUTE (THSTI), Faridabad (IN)

(72) Inventors: B. Ravindran, Bhubaneswar (IN); Diwakar Kumar Singh, Bhubaneswar (IN); Shailendra Asthana, Faridabad (IN); Sagar Gaikwad, Galveston, TX (US); Dileep Vasudevan, Bhubaneswar (IN); Narottam Acharya, Bhubaneswar (IN)

(73) Assignee: INSTITUTE OF LIFE SCIENCES, Bhubaneswar (IN)

( * ) Notice: Subject to any disclaimer, the term of this patent is extended or adjusted under 35 U.S.C. 154(b) by 394 days.

(21) Appl. No.: 18/253,739

(22) PCT Filed: Nov. 15, 2021

(86) PCT No.: PCT/IN2021/051070
§ 371 (c)(1),
(2) Date: May 19, 2023

(87) PCT Pub. No.: WO2022/107160
PCT Pub. Date: May 27, 2022

(65) Prior Publication Data
US 2024/0000786 A1 Jan. 4, 2024

(30) Foreign Application Priority Data
Nov. 20, 2020 (IN) ............................ 202031050500

(51) Int. Cl.
*A61K 31/519* (2006.01)
*A61K 31/357* (2006.01)
*A61K 31/40* (2006.01)
*A61K 31/422* (2006.01)
*A61P 43/00* (2006.01)

(52) U.S. Cl.
CPC .......... *A61K 31/519* (2013.01); *A61K 31/357* (2013.01); *A61K 31/40* (2013.01); *A61K 31/422* (2013.01); *A61P 43/00* (2018.01)

(58) Field of Classification Search
CPC .................................................... A61K 31/519
See application file for complete search history.

(56) References Cited

PUBLICATIONS

Deshpande et al., "Nitric Oxicde Modulators: An Emerging Class of Medicinal Agents," Indian Journal of Pharmaceutical Science 74: 487-497 (2012).
Minhas et al., "Inducible nitric oxide synthase inhibitors: A comprehensive update," Med. Res. Rev. 40: 823-855 (2020).

*Primary Examiner* — Yong S. Chong
(74) *Attorney, Agent, or Firm* — Jeffrey N. Townes; Cozen O'Connor

(57) ABSTRACT

The present invention discloses a pharmaceutical composition comprising 1-{3-[9-methoxy-7-(2-methoxyphenyl)-2,3,4,5-tetrahydro-1,4-benzoxazepine-4-carbonyl] phenyl}imidazolidin-2-one; N-tert-butyl-2-{N-[(furan-2-yl) methyl]-2-[5-(4-methylphenyl)-2H-1,2,3,4-tetrazol-2-yl] acetamido}-2-(4-hydroxyphenyl)acetamide; 3-[2-(2-{[(6-hydroxy-2,4-dioxo-1,2,3,4-tetrahydropyrimidin-5-yl) (4hydroxyphenyl) methyl]amino}-4-oxo-4,5-dihydro-1,3-thiazol-5-yl) acetamido]benzoic acid; 2-oxo-2-(1H-pyrrol-2-yl)ethyl 2-[(4-fluorophenyl)methoxy]benzoate; and 5-(3-{[(3-bromo-4-hydroxy-5 methoxyphenyl) methylidene] amino}-2 (butylimino)-2,3-dihydro-1,3-thiazol-4-yl)-2-hydroxybenzamide. The components are small molecule antagonists that increase the intracellular nitric oxide level by inhibiting the interaction between Nitric oxide synthase interacting proteins and inducible Nitric oxide synthase.

6 Claims, 9 Drawing Sheets

Specification includes a Sequence Listing.

(a) (b)

(a) (b)

(a)

(b)

COMPOSITION FOR ENHANCING INTRA-CELLULAR NITRIC OXIDE GENERATION

FIELD OF INVENTION

The present disclosure relates to the field of immunology. The present disclosure relates to a pharmaceutical composition comprising small molecules for enhancing the intracellular nitric oxide in vitro in human and mouse leukocytes and endogenous induction of nitric oxide in mice and their use for induction of anti-viral and anti-inflammatory host response.

BACKGROUND AND PRIOR ARTS OF THE INVENTION

Nitric oxide (NO) is a highly potent signaling molecule involved in a variety of physiological processes. NO is produced by neuronal nitric oxide synthase (nNOS or NOS1), inducible nitric oxide synthase (iNOS or NOS2) and endothelial nitric oxide synthase (eNOS or NOS3) which regulate nervous, immune and endothelial system functions respectively (Förstermann, U., and Sessa, W. C. (2012) European heart journal 33, 829-837Nitric oxide synthases: regulation and function).

A variety of biological functions such as inflammation, vasodilation, platelet aggregation/adhesion, leucocyte adhesion, vascular smooth muscle proliferation, angiogenesis and other physiological processes are mediated by Nitric Oxide (Niedbala, W., Besnard, A.-G., Jiang, H. R., Alves-Filho, J. C., Fukada, S. Y., Nascimento, D., Mitani, A., Pushparaj, P., Alqahtani, M. H., and Liew, F. Y. (2013) The Journal of Immunology 191, 164-170 Nitric Oxide-Induced Regulatory T Cells Inhibit Th17 but Not Th1 Cell Differentiation and Function; Niedbala, W., Alves-Filho, J. C., Fukada, S. Y., Vieira, S. M., Mitani, A., Sonego, F., Mirchandani, A., Nascimento, D. C., Cunha, F. Q., and Liew, F. Y. (2011) Proceedings of the National Academy of Sciences 108, 9220-9225. Regulation of type 17 helper T-cell function by nitric oxide during inflammation; Lundberg, J. O., Gladwin, M. T., and Weitzberg, E. (2015) Nature Reviews Drug Discovery 14, 623-641. Strategies to increase nitric oxide signalling in cardiovascular diseaseBogdan, C. (2015) Trends in immunology 36, 161-178. Nitric oxide synthase in innate and adaptive immunity: an update; Bogdan, C. (2001) Nature immunology 2, 907-916 Nitric oxide and the immune response 21.; Bauer, H., Jung, T., Tsikas, D., Stichtenoth, D., FRÖLICH, C., and Neumann, C. (1997) Immunology 90, 205-211 Nitric oxide inhibits the secretion of T-helper 1- and T-helper 2-associated cytokines in activated human Tcells'pa; Jon O. Lundberg, Mark T. Gladwin and Eddie Weitzberg, Strategies to increase nitric oxide signalling in cardiovascular disease,doi:10.1038/nrd4623, 7 Aug. 2015, Nature Reviews; Almudena Garcia-Ortiz and Juan M. Serrador, Nitric oxide Signaling in T Cell-Mediated Immunity, https://doi.org/10.1016/j.molmed.2018.02.002.; Wanda Niedbala, Beilei Cai, Haiying Liu, Nick Pitman, Lynda Chang and Foo Y. Liew, Nitric Oxide Induces CD4+ CD25+ Foxp3− regulatory T cells from CD4+CD25− T cells via p53, IL-2, and OX40, www.pnas.org/cgi/doi/10.1073/pnas.0703725104; Wanda Niedbala, Jose C. Alves-Filho, Sandra Y. Fukada, Silvio Manfredo Vieira, Akio Mitani, Fabiane Sonego, regulation of type 17 helper T-cell function by nitric oxide during inflammation, www.pnas.org/cgi/doi/10.1073/pnas.1100667108.).

More importantly, NO plays an integral role in defense against bacterial, viral and parasitic pathogens in immune cell signaling and biochemical pathways and in regulating pathways of host inflammation (Hassan Fahmi, Daniel Charon, Michelle mondange and Richard Chaby, Endotoxin-Induced Desensitization of mouse Macrophages is Mediated in part by Nitric Oxide Production, http://iai.asm.org/, Dec. 29, 2019.; Mirela B., Maria C. Almeida, Evelin C. Carnio and Luiz G. S. Branco, Role of nitric oxide in tolerance to lipopolysaccharide in mice, doi:10.1152/japplphysiol.01243.2004.; Devangi R. Mehta, Ali A. Ashkar, Karen L. Mossman, The nitric oxide pathway provides innate Antiviral protection in Conjunction with the Type 1 Interferon Pathway in Fibroblasts, doi:10.1371/journal.pone.0031688; Fabio Lisi, Alexander N. Zelikin and Rona Chandrawati, Nitric Oxide to Fight viral Infections, DOI: 10.1002/advs.202003895,2021.; Howlin, R. P., Cathie, K., Hall-Stoodley, L., Cornelius, V., Duignan, C., Allan, R. N., Fernandez, B. O., Barraud, N., Bruce, K. D., and Jefferies, J. (2017) Molecular Therapy 25, 2104-2116. Low-Dose Nitric Oxide as Targeted Anti-biofilin Adjunctive Therapy to Treat Chronic *Pseudononas aeruginosa* Infection in Cystic Fibrosis.; Jeney, V., Ramos, S., Bergman, M.-L., Bechmann, L, Tischer, J., Ferreira, A., Oliveira-Marques, V., Janse, C. J., Rebelo, S., and Cardoso, S. (2014) Cell Reports 8, 126-136 Control of disease tolerance to malaria by nitric oxide and carbon monoxide).

NO is produced at various concentrations (nm-μm) in cells by enzymatic action of NOS using L-arginine as substrate. Among the three isoforms, eNOS and nNOS are constitutively expressed while iNOS is inducible in immune cells during their activation. Synthesis and release of NO is tightly regulated by molecules involved in several regulatory pathways. Fine-tuning of NOS activity is mediated post-transnationally by protein-protein interactions.

Nitric oxide synthase interacting protein (NOSIP) has emerged as a central modulator of biological activity of NOS. NOSIP interacts with all three isoforms of NOS with high affinity and is co-expressed in cells (Dedio, J., König, P., Wohlfart, P., SCHROEDER, C., KUMMER, W., and MÜLLER-ESTERL, W. (2001) The FASEB Journal 15, 79-89 NOSIP, a novel modulator of endothelial nitric oxide synthase activity.; Dreyer, J., Schleicher, M., Tappe, A., Schilling, K., Kuner, T., Kusumawidijaja, G., Müller-Esterl, W., Oess, S., and Kuner, R. (2004) Journal of Neuroscience 24, 10454-10465 Nitric oxide synthase (NOS)-interacting protein interacts with neuronal NOS and regulates its distribution and activity). It inhibits synthesis of NO by relocating NOS from the plasma membrane to intracellular compartments thereby uncoupling NOS from plasma membrane caveolae (Dedio, J., König, P., Wohlfart, P., SCHROEDER, C., KUMMER, W., and MÜLLER-ESTERL, W. (2001) The FASEB Journal 15, 79-89 NOSIP, a novel modulator of endothelial nitric oxide synthase activity).

Expression, kinetics and regulation of NOSIP in mammalian cells and organs are largely unexplored. Therefore, NOSIP is a major NOS interacting protein that down-regulates biological activity of all three isoforms of nitric oxide synthases viz., nNOS, iNOS and eNOS. NOSIP indirectly regulates the level of NO produced by different cells/organs.

NO plays a central role in a wide range of pathological conditions such as infectious diseases, cardiovascular diseases, hypertensive pregnancies, rheumatoid arthritis, systemic lupus erythematous, multiple sclerosis, septic shock etc., (Förstermann, U., et al. (2016); Howlin, R. P., et al.

(2017)). Most of these diseases are associated with impaired NO production and/or activity. Decreased availability of NO has been attributed to imbalance between its synthesis and degradation (Förstermann, U., et al. (2016)). Consequently, many chemical NO donors have been designed for potential use for management of several pathologies (Schairer, D. O., Chouake, J. S., Nosanchuk, J. D., and Friedman, A. J. (2012) Virulence 3, 271-279 The potential of nitric oxide releasing therapies as antimicrobial agents). However, such NO donors have very limited clinical application since NO is unstable with very short half-life (Dreyer, J., Schleicher, M., Tappe, A., Schilling, K., Kuner, T., Kusumawidijaja, G., Müller-Esterl, W., Oess, S., and Kuner, R. (2004) Journal of Neuroscience 24, 10454-10465 Nitric oxide synthase (NOS)-interacting protein interacts with neuronal NOS and regulates its distribution and activity; Schairer, D. O., Chouake, J. S., Nosanchuk, J. D., and Friedman, A. J. (2012) Virulence 3, 271-279 The potential of nitric oxide releasing therapies as antimicrobial agents; Levine, A. B., Punihaole, D., and Levine, T. B. (2012) Cardiology 122, 55-68 Characterization of the Role of Nitric Oxide and its Clinical Applications; Reger, N. A., Meng, W. S., and Gawalt, E. S. (2017) Journal of functional biomaterials 8, 20 Antimicrobial Activity of Nitric Oxide-Releasing Ti-6Al-4V Metal Oxide; Fitzhugh, A. L., and Keefer, L. K. (2000) Free Radical Biology and Medicine 28, 1463-1469. Diazeniumdiolates:: Pro- and antioxidant applications of the "NONOates"; Li, B., Ming, Y., Liu, Y., Xing, H., Fu, R., Li, Z., Ni, R., Li, L., Duan, D., and Xu, J. (2020) Frontiers in Pharmacology 11, 923 Recent Developments in Pharmacological Effect, Mechanism and Application Prospect of Diazeniumdiolates; Arlene Bradley Levine, David Punihaole, T. Barry Levine, Characterization of the role of nitric oxide and its clinical Applications, DOI:10.1159/000338150,19 june, 2012; Maurizio Forte, Valeria Conti, Antonio Damato, Mariateresa Ambrosio, Annibale A. Puca, Targeting Nitric Oxide with Natural Derived Compounds as a Therapeutic Strategy in Vascular Diseases, http://dx.doi.org/10.1155/2016/7364138, Hindawi Publishing Corporation; David O. Schairer, Jason S. Chouake, Joshua D. Nosanchuk and Adam J. Friedmam, The Potential of nitric oxide releasing therapies as antimicrobial agents, http://dx.doi.org/10.4161/viru.20328.).

Nitric Oxide (NO) displays a variety of biological activity such as a) vasodilation b) anti-inflammation c) anti-thrombotic d) anti-proliferative e) neuroprotective f) anti-bacterial g) anti-viral effect etc., Thus induction of Nitric Oxide in vivo has been perceived to have several pharmacological benefits. Search for molecules that induce NO has been a major activity in the area of drug development. Currently the following approaches are being pursued—a) consumption or administration of Nitrate/Nitrite salts and their conversion into NO by bacterial nitrate reductase in the gut, b) Dietary supplementation of L-arginine to increase substrate levels for Nitric Oxide Synthase enzyme to generate more NO by cells, c) administration of chemical NO donors which have very short half-life. Such approaches are disclosed in WO1996016645A1 and US20210290663A1.

Therefore, there exists a need in the art for molecules that can induce Nitric Oxide production in the cells.

OBJECTS OF THE INVENTION

It is therefore an object of the present disclosure to propose a composition for increasing intracellular nitric oxide concentration.

It is an object of the present invention to demonstrate ability of NOSIP to interact with iNOS and inhibit its enzyme activity in a dose dependent manner to generate Nitric Oxide.

Another object of the invention is to demonstrate affinity of small molecules of the composition to interact with NOSIP for potential use as antagonists.

Another object of the invention is to induce human and mice cells to generate Nitric Oxide in vitro by treatment with Small Molecule 'NOSIP antagonists'.

Yet another object of the invention is to generate endogenous Nitric Oxide in mice by administration of Small Molecule 'NOSIP antagonists'.

Yet another object of the invention is to demonstrate up-regulation of type 1 Interferons viz., IFN-α and IFN-b genes and Inflammatory stimulatory genes (ISGs) in vitro by small molecule "NOSIP antagonists".

Still another object of the invention is to therapeutically use Small Molecule 'NOSIP antagonists' to inhibit generation of inflammatory cytokines in mice induced by administration of bacterial endotoxin, Lipopolysaccharide (LPS).

These and other objects and advantages of the invention will be apparent from the ensuing description.

SUMMARY OF THE INVENTION

According to this invention is provided a composition comprising five small molecules wherein the molecules inhibit nitric oxide synthase interacting proteins and inducible Nitric oxide synthase interaction.

In one embodiment, the present invention discloses a pharmaceutical composition for enhancing intracellular nitric oxide in a subject, the said composition comprising 1-{3-[9-methoxy-7-(2-methoxyphenyl)-2,3,4,5-tetrahydro-1,4-benzoxazepine-4-carbonyl]phenyl}imidazolidin-2-one; N-tert-butyl-2-{N-[(furan-2-yl)methyl]-2-[5-(4-methylphenyl)-2H-1,2,3,4-tetrazol-2-yl]acetamido}-2-(4-hydroxyphenyl)acetamide; 3-[2-(2-{[(6-hydroxy-2,4-dioxo-1,2,3,4-tetrahydropyrimidin-5-yl)(4hydroxyphenyl) methyl]amino}-4-oxo-4,5-dihydro-1,3-thiazol-5-yl)acetamido]benzoic acid; 2-oxo-2-(1H-pyrrol-2-yl)ethyl 2-[(4-fluorophenyl)methoxy] benzoate, and 5-(3-{[(3-bromo-4-hydroxy-5 methoxyphenyl) methylidene]amino}-2 (butylimino)-2,3-dihydro-1,3-thiazol-4-yl)-2-hydroxybenzamide.

In another embodiment, the present invention discloses a method of preparing the composition.

BRIEF DESCRIPTION OF THE ACCOMPANYING DRAWINGS

It is to be noted, however, that the appended drawings illustrate only typical embodiments of the present subject matter and are therefore not to be considered for limiting of its scope, for the invention may admit to other equally effective embodiments. The detailed description is described with reference to the accompanying figures. Some embodiments of system or methods in accordance with embodiments of the present subject matter are now described, by way of example, and with reference to the accompanying figures, in which:

FIG. 1 is a graphical representation of nitrite levels measured by Griess reagent demonstrating recombinant NOSIP inhibits Nitric Oxide Synthase (iNOS) enzyme activity in vitro.

FIG. 2 depicts inhibition of iNOS-NOSIP protein interaction by iNOS derived peptides. FIG. 2(*a*) depicts the iNOS and NOSIP purified protein (125 nM) interact to each other in SPR analysis as shown in pink at top of graph. These interactions was inhibited in presence of different iNOS peptides (250 nM) viz; PP1—red line, PP2—sky blue line at bottom of graph, PP3—blue line and PP4—green line. FIG. 2(*b*) demonstrates dose dependent binding inhibition of NOSIP protein in the presence of iNOS peptide which shows kinetics of NOSIP binding (1000 nM to 62.5 nM, top to bottom) in presence of 250 nM iNOS PP2. The Ka=$5.36^{e+03}$, Kd=$2.65^{e-03}$ KD=$4.95^{e-07}$M was obtained in Kinetic—Langmuir analysis.

FIG. 3 depicts Calorimetric titration of rNOSIP with 18 mer iNOS peptide (PP2).

FIG. 4 depicts Specific Plasmon Resonance Analysis of rNOSIP (250 nM) in presence of small molecules NOSIP antagonists (1 uM). FIG. 4(A). The recombinant NOSIP protein (250 nM) binding in pink line at top of graph, blue line—binding of protein in presence of small molecule 2, sky blue line—small molecule 3, green line-small molecule 5 and red line—small molecule 4. (B) Pink line—rNOSIP protein binding, green line—small molecule 1, sky blue line—small molecule 7, blue line—small molecule 9, red line—small molecule 6 (C) Pink line—rNOSIP protein binding, green line—small molecule 10, sky blue line—small molecule 12, blue line—small molecule 13, red line—small molecule 11. The best binding molecules (n=5) kept for further analysis. (FIGS. 4(D-G)) shows Isothermal Titration Calorimetry for all the five small molecules NOSIP antagonists and its kinetics are listed in table.

FIG. 5 depicts small molecule NOSIP antagonists potentiates TLR ligands-induced NO production in Murine Bone marrow derived mononuclear (BMDM) cells in vitro.

FIG. 5 (left panel) shows that small molecules combination (tested at two concentrations viz., 0.01 uM and 0.1 uM) in vitro and incubated overnight at 37C. The SM were incubated with or without the following TLR ligands: LPS, b-glucan, flagellinh, Pam3Csk, Poly IC, and CpG DNA. The SM generates Nitric Oxide in a dose dependent manner and also potentiate Nitric Oxide production in murine BMDM treated with TLR ligands. The right panel in FIG. 5 is a replication of the same experiment as described above.

DETAILED DESCRIPTION OF THE INVENTION

Figure 1:
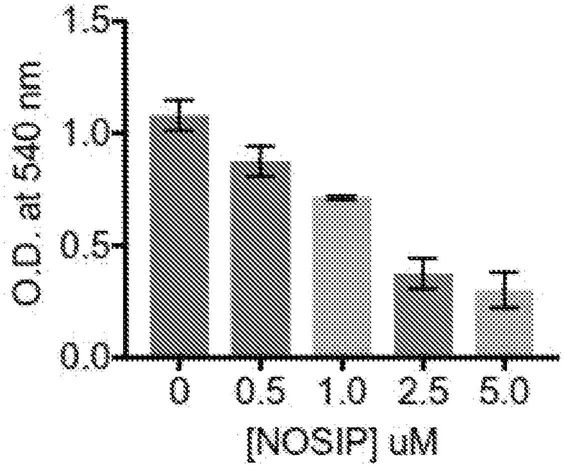

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the forms disclosed, but on the contrary, the disclosure is to cover all modifications, equivalents, and alternatives falling within the scope of the disclosure.

The terminology used herein is to describe particular embodiments only and is not intended to be limiting of example embodiments. As used herein, the singular forms "a", "an" and "the" are intended to include the plural forms as well, unless the context indicates otherwise.

It will be further understood that the terms "comprise", "comprising", "includes" and/or "including" when used herein, specify the presence of stated features, steps, operations, elements and/or components, but do not preclude the presence or addition of one or more other features, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

The term "equimolar concentration" implies having same molar concentration of solute in a solution. In the context of the present invention, the said term denotes the molar concentration of each of the 5 small molecule antagonists is same i.e., they are added in the ratio of 1:1:1:1:1 for preparing the stock solution and later suspending in phosphate buffer saline solution.

The term "MER" denotes the number of amino acid residues. 18 mer means a peptide (PP2) containing 18 amino acids.

According to the present disclosure, is provided a pharmaceutical composition comprising:

1-{3-[9-methoxy-7-(2-methoxyphenyl)-2,3,4,5-tetrahydro-1,4-benzoxazepine-4-carbonyl]phenyl}imidazolidin-2-one;

N-tert-butyl-2-{N-[(furan-2-yl)methyl]-2-[5-(4-methylphenyl)-2H-1,2,3,4-tetrazol-2-yl]acetamido}-2-(4-hydroxyphenyl)acetamide;

3-[2-(2-{[(6-hydroxy-2,4-dioxo-1,2,3,4-tetrahydropyrimidin-5-yl)(4hydroxyphenyl) methyl]amino}-4-oxo-4,5-dihydro-1,3-thiazol-5-yl)acetamido]benzoic acid;

2-oxo-2-(1H-pyrrol-2-yl)ethyl 2-[(4-fluorophenyl)methoxy]benzoate; and 5-(3-{[(3-bromo-4-hydroxy-5 methoxyphenyl) methylidene]amino}-2 (butylimino)-2,3-dihydro-1,3-thiazol-4-yl)-2-hydroxybenzamide.

In an embodiment of the present disclosure, the components are small molecule antagonists that block the interaction between Nitric oxide synthase interacting proteins and inducible Nitric oxide synthase.

In one embodiment of the present disclosure, the components are present in an equimolar concentration in phosphate buffer saline.

In another embodiment of the present disclosure, the components either alone or in combination enhances Nitric Oxide level at 0.1 and 0.01 μM concentrations.

In yet another embodiment, the present disclosure provides a method for preparing the composition comprising selection of five different small molecules (viz; MCULE3765839647, MCULE8395438746, MCULE8094061955, MCULE8469877005, and MCULE4640800528) from chemical library, preparing 1M stock solution by dissolving 5 mg of the powder in 1 ml dimethyl sulfoxide, preparing cocktail of 1M solution by mixing 0.2 ml of each of the small molecule components as claimed in claim 1 making a total volume of 1 ml and storing at −20 °C, preparing 1 ml cocktail of 100 uM stock solution in phosphate buffer saline by adding 0.1 ml of 1M stock in DMSO to 0.9 ml of phosphate buffer saline and storing for further use in −20 C in aliquots of 100 μl each, thawing 100 μM stock solution and addition of small molecule antagonists at different concentrations in phosphate buffer solution.

The small molecules are designated as 'NOSIP antagonists' and an equi-molar mixture of all 5 Small Molecule 'NOSIP antagonists' were used for biological experiments. Incubation of human peripheral blood mononuclear cells (PBMC) or murine Bone marrow derived Mononuclear cells (BMDM) in vitro with "NOSIP antagonists" induced production of Nitric Oxide by the cells. 'NOSIP antagonists' further potentiated TLR (Toll like receptors) agonists (LPS, PGN, CpG DNA, Flagellin) induced synthesis of Nitric Oxide by the above cells. A single dose of 100 ul-200 ul of 100 uM solution of "NOSIP antagonists" by intra-peritoneal route to mice resulted in production of Nitric Oxide in vivo as shown by elevated levels of Nitrate/Nitrite in plasma and peritoneal cavity in BALB/c mice. Mice administered with 100 ul of 100 uM "NOSIP antagonists" followed by injection of 5 mg/kg body weight of bacterial Endotoxin (Lipopolysaccharide, that induces inflammatory cytokines in circulation) resulted in decreased levels of inflammatory cytokines such as TNF-α and IL-1β. Macrophage cell line RAW incubated with "NOSIP antagonists" in vitro culture for 10 hrs at 37 C and analysed by Q-RT-PR were found to significantly activate for anti-viral genes viz., different subtypes of Interferon-a, Interferon-b, Interferon stimulated genes (ISGs).

The invention is now illustrated by way of non-limiting examples. The examples are intended to be purely exemplary of the invention, should therefore not be considered to limit the scope invention in any way. While the present invention has been described in terms of its specific embodiments, certain modifications and equivalents will be apparent to those skilled in the art and are intended to be included within the scope of the present invention.

EXAMPLES

Example 1

Cloning, Expression and Purification of iNOS and NOSIP Proteins and their Inhibiting Interaction The human iNOS oxygenase domain (SEQ ID No.: 24) containing 424 nucleotide sequence and NOSIP gene (SEQ ID No.: 23) containing 301 nucleotide sequences were synthesized by GenScript and cloned in pET22b expression vector. The recombinant pET22b: iNOS and pET22b: NOSIP plasmid was used to transform competent *E. coli* BL21 (DE3) cells. The proteins were over expressed using 0.2 mM IPTG at 25 °C. The harvested cells were resuspended and sonicated in 20 mM Tris-HCl, pH 7.5, 200 mM NaCl, 0.05% Triton X-100 and protease inhibitor (Sigma). The expressed proteins were purified by nickel nitrilotriacetic acid column using 250 mM imidazole and gel filtration chromatography. The protein was quantified by Bradford assay (Sigma) and integrity of purified protein was checked on 12% SDS-PAGE.

In a calorimetric assay increasing concentrations of recombinant NOSIP were mixed with recombinant iNOS along with substrate L-Arginine and the resultant product, nitrate was quantified by using Griess reaction kit. The red bar in FIG. 1 shows iNOS (0.5 μM) enzyme activity in absence of NOSIP and blue bars shows inhibition of iNOS (0.5 μM) enzyme activity in presence of different concentration of NOSIP (0.5 to 5 μM). Statistical significance was assessed by one way ANOVA, Tukey& #39;s Multiple Comparison Test. It was observed that recombinant NOSIP inhibits enzyme activity of iNOS.

Example 2

Figure 2:
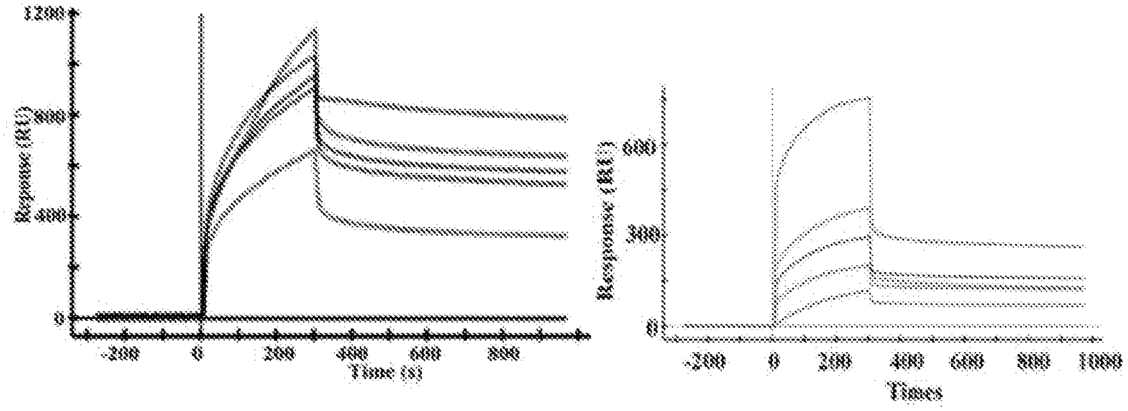
Figure 3:
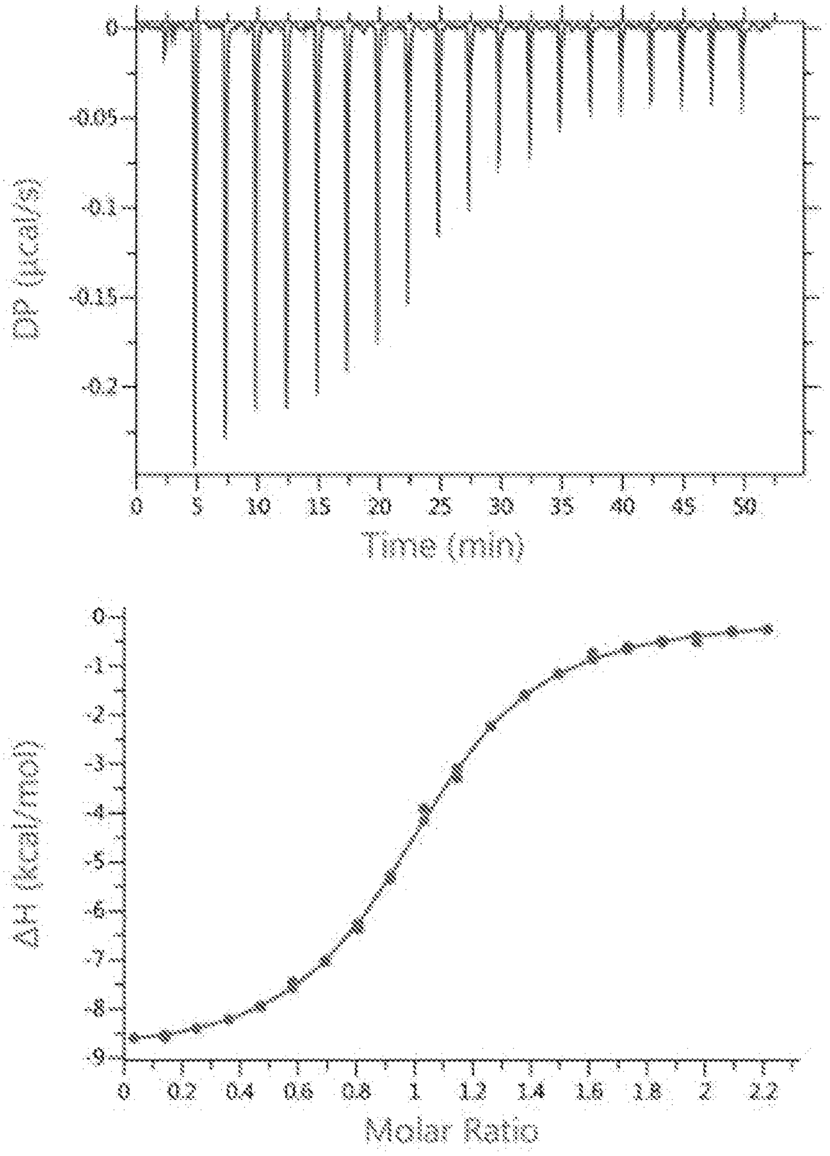

Identification of iNOS Peptides that Block Interaction Between iNOS and NOSIP:

3-D structures of iNOS and NOSIP were analyzed by 7 different tools (PIPER, SWORM DOCK, PyDOCK, Z-DOCK, HADDOCK, ATTRACT, CLUSPRO) that resulted in prediction of four different iNOS peptides that can interfere with their interactions. The predictions were tested for validation by Specific Plasmon Resonance (SPR). One of the peptides (Peptide-2 abbreviated as PP-2) (SEQ ID No: 26) was found to block significantly interaction between recombinant iNOS and NOSIP as shown by SPR. The other 3 peptides (Peptide-1, SEQ ID No: 25), (Peptide3, SEQ ID No: 27), and (peptide-4, SEQ ID No: 28) were less efficient in inhibiting interaction between iNOS and NOSIP as shown in FIG. 2(*a*). The FIG. 2(*b*) titration of peptide 2 by SPR demonstrating a dose dependent interaction between NOSIP and iNOS peptide 2. FIG. 3 shows interaction between NOSIP and iNOS peptide2 by Isothermal Titration (ITC). NOSIP and iNOS peptide (PP2) binding was measured by titrating 10 μM iNOS peptide in the chamber with 150 μM rNOSIP in syringe at 25 °C. Top panel, raw heating power over time; Bottom panel, fit of integrated injection enthalpy over the mole ratio of the reactants. The resulting isotherms and binding kinetics was obtained by the application of ITC instrumental software, N=0.993, KD (nM)=493±63.2, ΔH (Kcal/mol)=−9.07±0.251, −TΔS (Kcal/mol)=0.459, ΔG (Kcal/mol)=−8.61.

Detailed methods used for the above analysis are the following:

Bimolecular Interaction by Surface Plasmon Resonance (SPR):

Four different iNOS peptides were synthesized commercially by China peptides and iNOS peptides were used for molecular interaction studies with immobilized recombinant iNOS purified protein. The iNOS peptides mediated inhibition of rNOSIP and riNOS protein association in Bio-Rad XPR 36 surface plasmon resonance biosensor instrument. About 3 μg/ml of iNOS was immobilized on GLC chip by amine coupling method as suggested by manufacturer's instructions. 250 nM of iNOS peptides was used for inhibition assay with immobilized ligand(recombinant iNOS) in SPR analysis. Similar condition and concentration of small molecules were used for inhibition of recombinant protein association with immobilized ligand. It inhibited the association of rNOSIP and r iNOS purified protein significantly in this study. The rNOSIP protein was incubated with iNOS derived peptide/small molecules for 30 minutes in ice for inhibition assay before the SPR application in our study. The molecular interaction was carried out at 20 °C and kinetic parameters were determined, after fitting the association and dissociation curves to a 1:1 (Langmuir)-binding model. An activated channel without immobilized ligand was used to evaluate nonspecific binding. The response curves were also recorded on control surfaces. Results were calculated after subtraction of the control values using the ProteOn Manager software.

SPR Data Analysis:

The collected sensorgram data were processed by reference subtraction using double-referencing with the in-line blank buffer. The integrated ProteOn Manager software was used to fit the data with the Langmuir model describing a 1:1 binding stoichiometry. Ka is the association rate constant, Kd is the dissociation rate constant, and KD is the equilibrium dissociation constant, defined by the Kd/Ka ratio for the analytes-ligand binding.

Isothermal Titration Calorimetry (ITC):

The 18 mer iNOS peptide (PP2) and small molecules were used for physical association of molecules in calorimetric analysis. The molecular association leads to thermodynamics changes such as Gibb's free energy change (ΔG), entropy change (ΔS), enthalpy change (ΔH) and number of binding sites (N) in interacting solution were investigated by isothermal calorimetry MICROCAL PEQ (Malvern) at 25 °C. The sample cell were filled with peptides, small molecules and the reference cell was filled with 25 mM HEPES and 150 mM Sodium chloride, pH=7 and the syringe was filled with NOSIP solution (200 μM). The experiment consisted of multiple injections and each injection contained 1.5 μl of binding solution (recombinant NOSIP solution) with 120 second spacing time between subsequent injections. Sequential titrations were carried out and the sample solution was continuously stirred at 270 rpm by the rotating paddle attached to the syringe needle. Multiple injections of NOSIP made into the sample cell containing interacting solution of peptide and small molecules. The titration curves were analyzed using the analysis software provided with the calorimeter.

Example 3

Identification of Small Molecules that Mimic iNOS Peptide 2 and Chemical Formulae and Structure 5 Small Molecules 'NOSIP Antagonists':

Using Peptide 2 of iNOS that significantly inhibited interaction between iNOS and NOSIP in SPR (as demonstrated in FIGS. 2 and 3), 12 different small molecules designated as CC1 to CC13 (with the exception of CC8) were selected by in silico methods using a virtual chemical library of 1.6 million molecules. The small molecules NOSIP Antagonists were identified by studying their interaction with high affinity to NOSIP as shown by SPR.

Detailed Description of SPR and ITC for SM:

The 18 mer iNOS peptide (PP2) and five small molecules were used to analyze physical association in calorimetric analysis. The molecular association leads to thermodynamics changes such as Gibb's free energy change (ΔG), entropy change (ΔS), enthalpy change (ΔH) and number of binding sites (N) in interacting solution were investigated by isothermal calorimetry MICROCAL PEQ (Malvern) at 25 °C The sample cell were filled with peptides, small molecules and the reference cell was filled with 25 mM HEPES and 150 mM Sodium chloride, pH=7 and the syringe was filled with NOSIP solution (200 μM). The experiment consisted of multiple injections and each injection contained 1.5 μl of binding solution with 120 second spacing time between subsequent injections. Sequential titrations were carried out and the sample solution was continuously stirred at 270 rpm by the rotating paddle attached to the syringe needle. Multiple injections of NOSIP made into the sample cell containing interacting solution of peptide and small molecules. The titration curves were analyzed using the analysis software provided with the calorimeter. The SM binding affinity with NOSIP is described below in table below and it indicates the following trends in terms of hierarchy viz, CC4>CC11>CC6>CC5>CC13>Peptide 2 (iNOS). The biophysical parameters observed for the 5 small molecule designated as NOSIP Antagonists' are shown in Table 1 below:

TABLE 1

| Small Molecules (Cell) | rNOSIP (Syringe) | N (Sites) | KD (nM) | ΔH (Kcal/mol) | −TΔS (Kcal/mol) | ΔG (Kcal/mol) | Fold Change (KD) |
|---|---|---|---|---|---|---|---|
| MCULE-4640800528 | NOSIP | 1.04 | 420 ± 57.5 | −8.54 ± 0.255 | −0.159 | −8.70 | 0.766 |
| MCULE-8469877005 | NOSIP | 0.794 | 535 ± 80.8 | −29.3 ± 1.12 | 20.8 | −8.56 | 0.976 |
| MCULE-3765839647 | NOSIP | 0.989 | 524 ± 64.9 | −27.3 ± 1.11 | 19.8 | −7.5 | 0.956 |
| MCULE-8094061955 | NOSIP | 0.993 | 493 ± 63.2 | −9.07 ± 0.251 | 0.459 | −8.61 | 0.899 |
| MCULE-8395438746 | NOSIP | 0.864 | 542 ± 54.9 | −28.5 ± 0.694 | 20.0 | −8.55 | 0.989 |
| iNOS-Peptide2 | NOSIP | 1.09 | 548 ± 81.1 | −8.44 ± 0.271 | −0.10 | −8.54 | 1 |

The structures for 5 selected SM NOSIP Antagonists are shown below in Table 2:

TABLE 2

| SN | Compound Name | Molecule ID/ Matched product/Assign Name | Structure | Mass |
|---|---|---|---|---|
| 1 | N-({1H,4H,5H,6H-cyclopenta[c]pyrazol-3-yl}methyl)-2[(2-methoxy-4-methylphenoxy) methyl]-1,3-oxazole-4-carboxamide | MCULE-4640800528/ P-504631944/ CC4 | 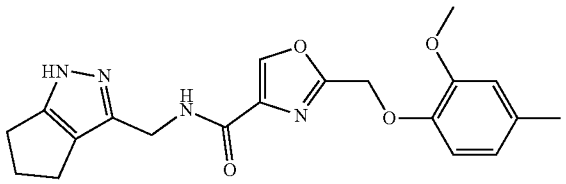 [SMILES: COc1cc(C)ccc1OCc1nc(C(=O)NCc2n[nH]c3c2CCC3)co1] | 382.4 |
| 2 | N-tert-butyl-2-{N-[(furan-2-yl)methyl]-2-[5-(4-methylphenyl)-2H-1,2,3,4-tetrazol-2-yl]acetamido}-2-(4-hydroxyphenyl) acetamide | MCULE-8469877005/ P-6260656/ CC5 | 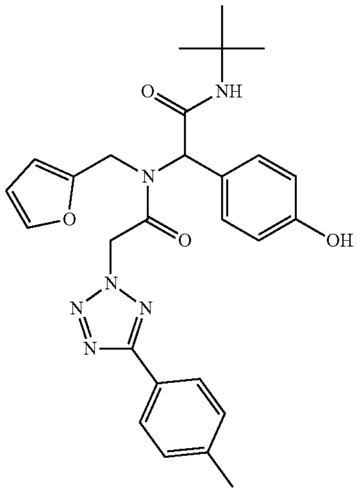 [SMILES: Cc1ccc(-c2nnn(CC(=O)N(Cc3ccco3)C(C(=O)NC(C)(C)C)c3ccc(O)cc3)n2)cc1] | 502.6 |
| 3 | 4-(2-{[2-(3,4-dichlorophenyl)-2-oxoethyl]sulfanyl}-4-oxo-3H,4H-thieno[3,2-d]pyrimidin-3-yl)-N-[2-(4-sulfamoylphenyl) ethyl]butanamide | MCULE-3765839647/ P-449585363/ CC6 | 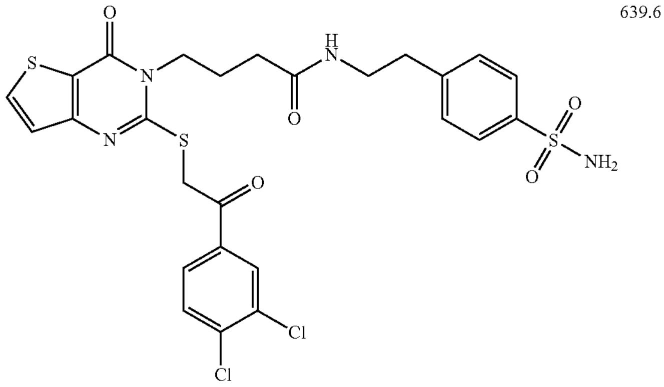 | 639.6 |

TABLE 2-continued

| SN | Compound Name | Molecule ID/ Matched product/Assign Name | Structure | Mass |
|---|---|---|---|---|
| 4 | ({2-chloro-5-[ethyl(phenyl) sulfamoyl]phenyl} carbamoyl)methyl 2-({[(2H-1,3-benzodioxol-5-yl)carbamoyl] methyl}sulfanyl) benzoate | MCULE-8094061955/ P-17494584/ CC11 | 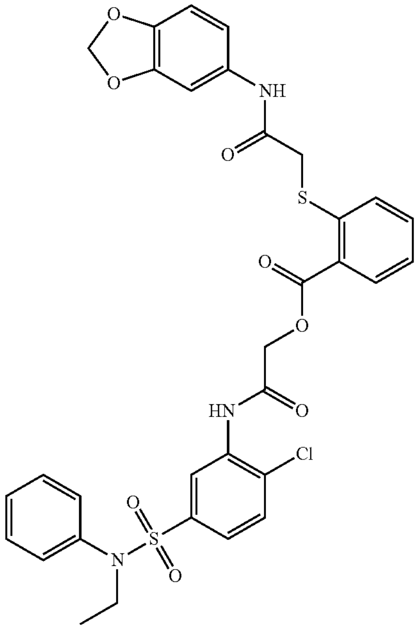 [SMILES: CCN(c1ccccc1)S(=O)(=O)c1ccc(Cl)c(NC(=O)COC(=O)c2ccccc2SCC(=O)Nc2ccc3c(c2)OCO3)c1] | 682.2 |
| 5 | 5-(3-{[(3-bromo-4-hydroxy-5-methoxyphenyl) methylidene] amino}-2-(butylimino)-2,3-dihydro-1,3-thiazol-4-yl)-2-hydroxybenzamide | MCULE-8395438746/ P-17901669/ CC13 | 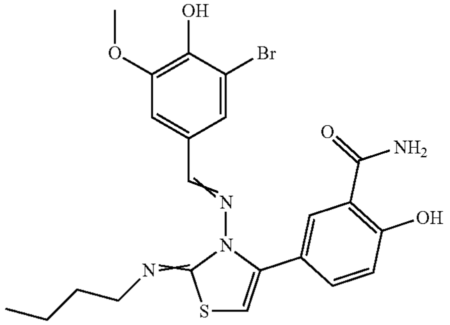 [SMILES: CCCCN=c1scc(-c2ccc(O)c(C(N)=O)c2)n1N=Cc1cc(Br)c(O)c(OC)c1] | 519.4 |

Figure 4:
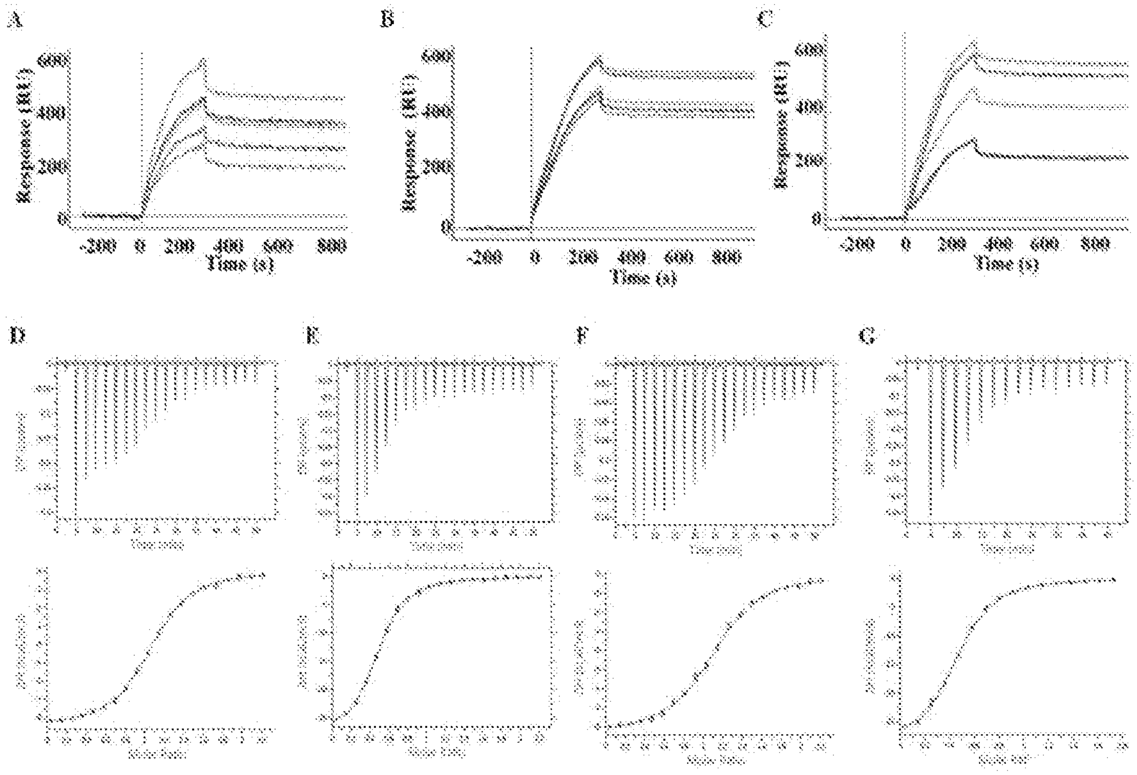

Kinetic parameter of bi-molecular interaction of between iNOS and NOSIP in the presence and absence of 5 small molecules as shown by SPR. FIGS. 4(*a*) to 4(*g*) shows details of SPR and ITC for all the five SM NOSIP Antagonists. The molecules inhibit the binding of NOSIP with iNOS ligand (FIG. 4 (*a*)) in presence of CC2, CC3, CC4, CC5 (FIG. 4 (*b*)) In presence of CC1, CC6, CC7 and CC9 (FIG. 4 (*c*)) In presence of CC10, CC11, CC12 and CC13. The same molecules were used for NOSIP binding assay in ITC (FIG. 4(*d*)) Binding of CC4, (FIG. 4(*e*)) Binding of CC5 (FIG. 4(*f*)) Binding of CC6 (FIG. 4(*g*)) Binding of CC13.

The five small molecules bind with NOSIP and inhibit the association of recombinant NOSIP and recombinant iNOS. The rNOSIP protein was incubated with iNOS derived peptide or small molecules for 30 minutes in ice prior to SPR application. The molecular interaction was carried out at 20 °C and kinetic parameters were determined, after fitting the association and dissociation curves to a 1:1 (Langmuir)-binding model. An activated channel without immobilized ligand (recombinant iNOS) was used to evaluate nonspecific binding. The response curves were also recorded on control surfaces. Results were calculated after subtraction of the control values using the ProteOn Manager software.

The collected sensorgram data were processed by reference subtraction using double-referencing with the in-line blank buffer. The integrated ProteOn

TABLE 3

| Analytes | Ligand | Ka(1/Ms) | Kd(1/s) | KD (M) | Fold Change (KD) |
|---|---|---|---|---|---|
| NOSIP | iNOS | $9.57e^{+04}$ | $6.81e^{-04}$ | $7.11e^{-09}$ | $1.439e^{-3}$ |
| rNOSIP + iNOS peptide2 | r iNOS | $5.36e^{+02}$ | $2.65e^{-03}$ | $4.94e^{-06}$ | 1 |
| rNOSIP + MCULE-4640800528 | r iNOS | $5.63e^{-01}$ | $4.9e^{-04}$ | $8.70e^{-04}$ | $1.761e^{+2}$ |
| rNOSIP + MCULE-8469877005 | r iNOS | $8.22e^{-01}$ | $4.83e^{-04}$ | $5.88e^{-04}$ | $1.190e^{+2}$ |
| rNOSIP + MCULE-3765839647 | r iNOS | $8.07e^{-01}$ | $5.68e^{-04}$ | $7.04e^{-04}$ | $1.425e^{+2}$ |
| rNOSIP + MCULE-8094061955 | r iNOS | $6.7e^{-01}$ | $5.42e^{-04}$ | $8.09e^{-04}$ | $1.637e^{+2}$ |

TABLE 3-continued

| Analytes | Ligand | Ka(1/Ms) | Kd(1/s) | KD (M) | Fold Change (KD) |
|---|---|---|---|---|---|
| rNOSIP + MCULE-8395438746 | r iNOS | $8.35e^{-01}$ | $4.53e^{-04}$ | $5.43e^{-04}$ | $1.099e^{+2}$ |

Manager software was used to fit the data with the Langmuir model describing a 1:1 binding stoichiometry. Ka is the association rate constant, Kd is the dissociation rate constant, and KD is the equilibrium dissociation constant, defined by the Kd/Ka ratio for the analytes—ligand binding. The Ka, Kd and KD values of the inhibiting interaction between the small molecules and NOSIP and iNOS are shown in table 3 below.

The different Small Molecules interacted with NOSIP and resulted in inhibition of iNOS-NOSIP protein interaction kinetics in SPR analysis. The inhibition hierarchy of the small molecules were as follow: CC4>CC11>CC6>CC5>CC13>iNOS Peptide 2.

Example 4

Figure 5:
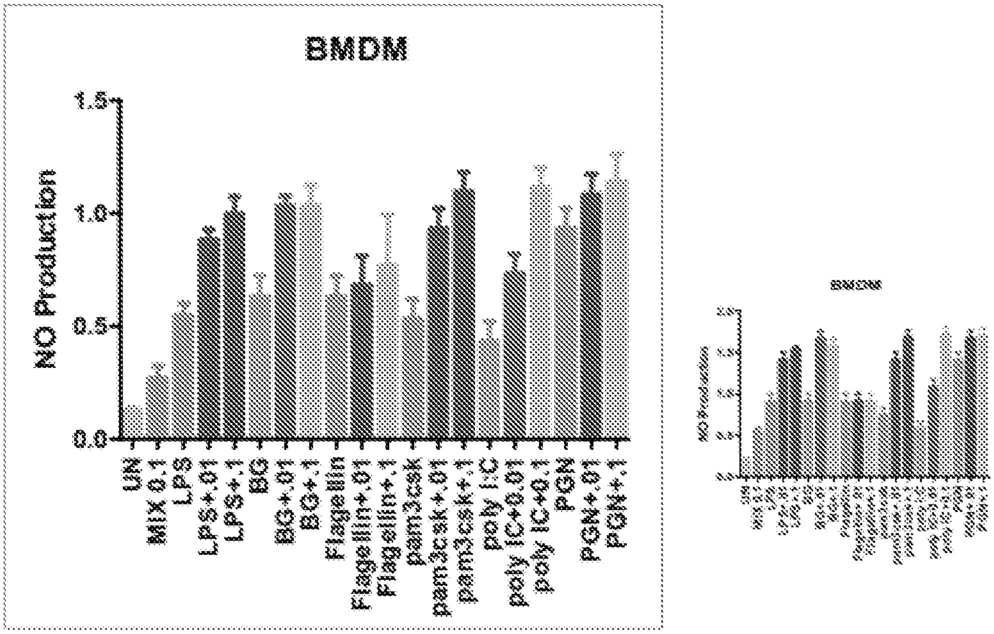

Evaluation of Bio-Activity of SM 'NOSIP Antagonists' for Induction of Nitric Oxide In Vitro by Murine BMDM as Estimated by Nitrite Production by Calorimetry:

Murine Bone marrow derived mononuclear cells (BMDM—1 million cells per ml) were treated with or without NOSIP antagonists (equimolar concentration of a mixture of all 5 small molecule antagonists) at 0.1 and 0.01 μM concentrations for 30 min followed by addition of LPS (1 μg/ml), β-glucan (5 μg/ml), flagellin (200 ng/ml), Pam3CSK4 (100 ng/ml), poly I:C (50 μg/ml), and PGN (10 μg/ml) in triplicate wells and incubated for 24 h at 37 °C. The culture supernatants were analysed by calorimetry for nitrite concentration using Griess reagent. The results (shown in FIG. 5(*b*)) reveals induction of NO by 'NOSIP antagonists' at 10.1 and 0.01 uM concentrations. TLR agonists mediated induction of NO were further potentiated by pre-treatment of cells with 'NOSIP antagonists'. The results are shown in FIG. 5 (the left and right panels are two set of experiments)

Example 5

Figure 6:
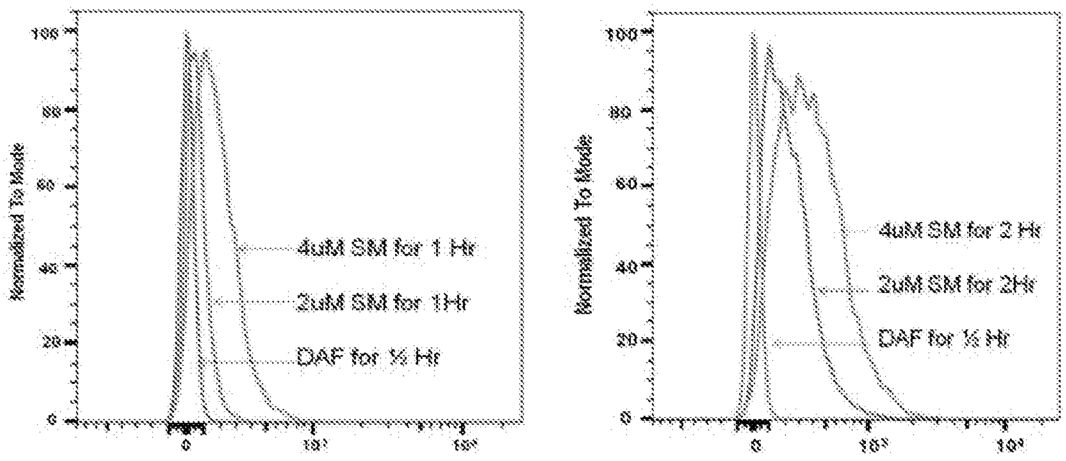
FIG. 6 depicts flow cytometry data and DAF-FM staining data for evaluation of Bio-activity of SM 'NOSIP antagonists' for induction of Nitric Oxide in vitro by murine BMDM.

Evaluation of Bio-Activity of SM 'NOSIP Antagonists' for Induction of Nitric Oxide In Vitro by Murine BMDM by Flow Cytometry:

Bone marrow cells single cell suspension, small molecules treatment and DAF-FM (4-Amino-5-methylamino-2',7'-difluorofluorescein diacetate) staining. The mouse femurs were aseptically isolated in Dubleco's phosphate buffer saline solution and kept immediately on ice. The muscles and residue tissues surrounding the femur were removed with sterile forceps and scissors. The femurs cut at both ends with sharp sterile scissors and marrow cells were flushed out using 26 gauge needle with ice cold DPBS. The collected sample was filtered through 70 m nylon cell strainer placed in a 50 ml falcon conical tube. The cells were washed and replaced with complete DMEM media by repeated centrifugation at 300 g for 10 minutes. The bone marrow cells were counted with a haemocytometer and $10^6$ cells/ml were used for small molecules cocktail treatment in this studies. Further, titration of 2 and 4 uM concentration of cocktails for 1 h and 2 h was carried out. The treated cells were further incubated with 10 uM DAF-FM for 30 minutes at 5% CO2 at 370C. The cells were washed with DMEM incomplete media and further incubated with fresh complete DMEM media. The further incubation of cells for 30 minutes allowed complete de esterification. The cells were lysed/fixed with BD lysis/permeabilization buffer before the flow cytometer analysis at 495 nM/515 nM. The results are shown in FIG. 6.

Example 6

Figure 7:
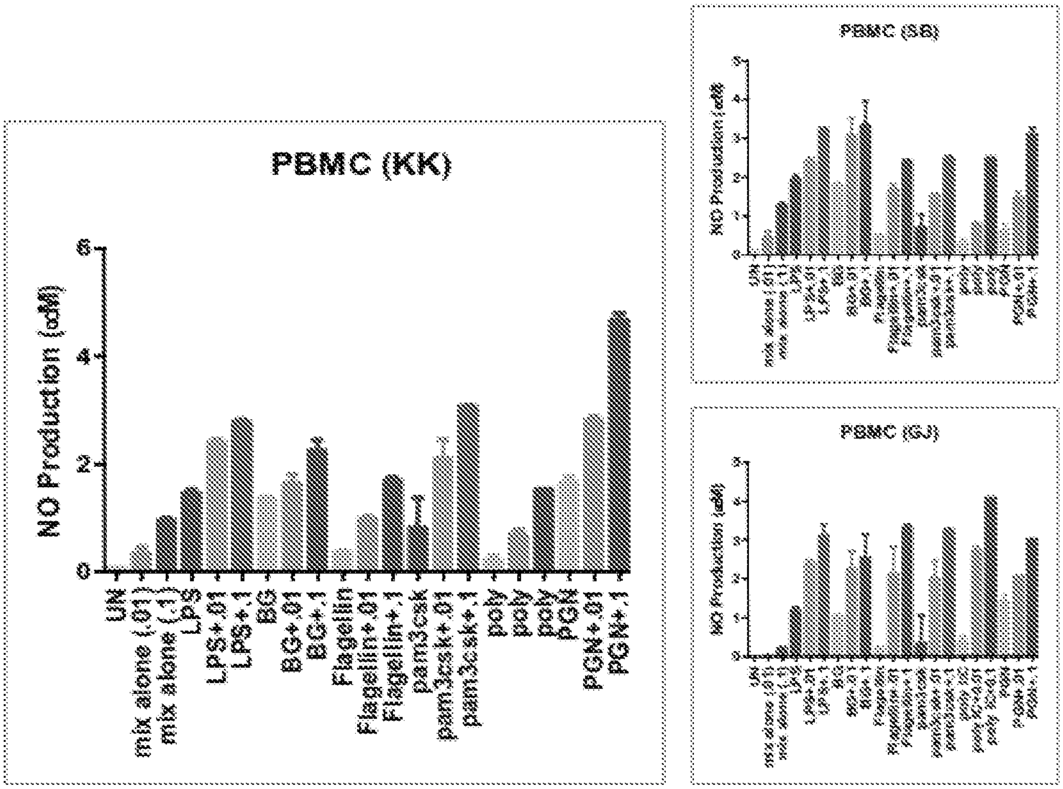
FIG. 7 illustrates small molecule NOSIP antagonists potentiates TLR ligands-induced NO production in Human peripheral blood mononuclear cells (PBMC).

Evaluation of Bio-Activity of SM 'NOSIP Antagonists' for Induction of Nitric Oxide In Vitro by Normal Human PBMC:

Normal human peripheral blood mononuclear cells (PBMC—1 million cells/ml) were treated with or without NOSIP antagonists (equimolar concentration of a mixture of all 5 small molecule antagonists) at 0.1 and 0.01 μM concentrations for 30 min followed by addition of LPS (1 μg/ml), β-glucan (5 μg/ml), flagellin (200 ng/ml), Pam3CSK4 (100 ng/ml), poly I:C (50 μg/ml), and PGN (10 μg/ml) in triplicate wells and incubated for 24 h at 37 °C. The culture supernatants were analysed by calorimetry for nitrite concentration using Griess reagent. The results (shown in FIG. 3 below) reveals induction of NO by 'NOSIP antagonists' at 10.1 and 0.01 uM concentrations. TLR agonists mediated induction of NO were further potentiated by pre-treatment of cells with 'NOSIP antagonists'. The results are shown in FIG. 7.

Example 7

Figure 8:
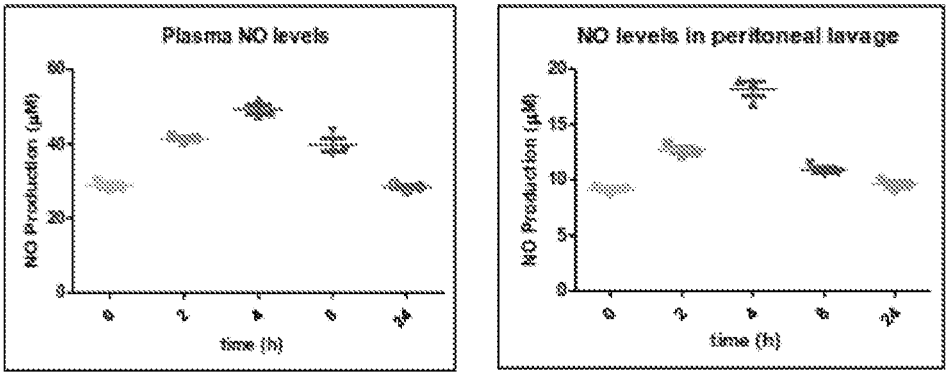
FIG. 8 illustrates nitrite estimation in mouse plasma/peritoneal lavage by Griess reaction on administration of SM NOSIP Antagonists.

Kinetics of In Vivo Nitric Oxide Induction by SM 'NOSIP Antagonists':

A mixture of all 5 Small molecule 'NOISP antagonists' were injected by intra-peritoneal route (100 μl/mouse of 100 mM) and groups of mice were sacrificed at different time points and plasma and peritoneal lavage were harvested and nitrite levels were quantified using Griess reagent. The levels are shown in FIG. 8—plasma (left) and in Peritoneal fluid (right) at different time points. The Nitrite levels reached a peak at 4 hrs post administration and normal levels were restored at 24 hrs.

Example 8

Figure 9:
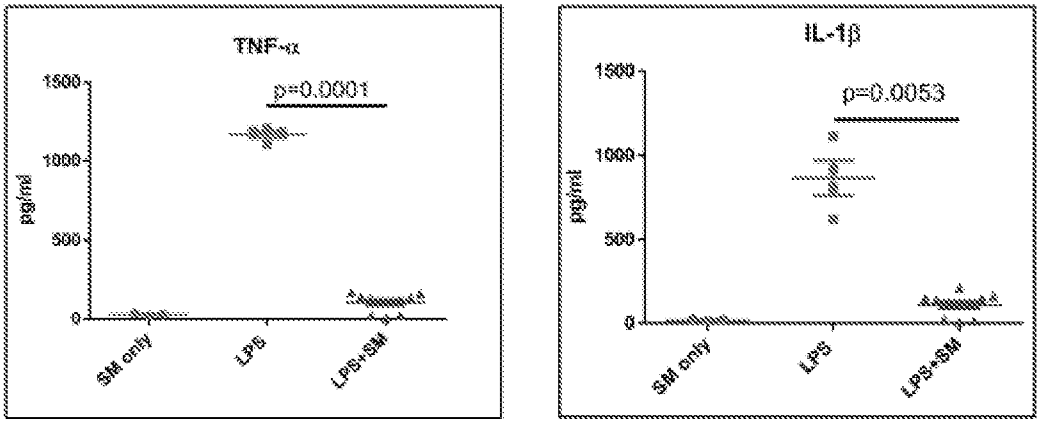
FIG. 9 depicts ELISA results reflecting pre-treatment of mice with 'NOSIP Antagonists' blocked induction of inflammatory cytokines such as TNF $\alpha$ and IL1-$\beta$ by LPS.

SM 'NOSIP Antagonists' Inhibit In Vivo Induction of Inflammatory Cytokines (TNF-α and IL-1b) by LPS in Mice:

Six to eight-week-old male C57BL/6 mice were intraperitoneally injected with 200 μl of 100 μM SM 'NOSIP Antagonists', prepared by mixing equimolar concentration of five small molecules in PBS before each experiment. After 2 hrs, mice were administered 5 mg/Kg of LPS and after two hours the animals were euthanized, and blood was collected by cardiac puncture. Plasma levels of inflammatory cytokines TNFα, and IL-1β were measured using commercially available ELISA kits, as per the manufacturer's instruction (ebioscience, USA; TNFα #501128954; IL-1β #501129749). Pre-treatment of mice with 'NOSIP Antagonists' blocked induction of inflammatory cytokines by LPS. The results are shown in FIG. 9.

Example 9

Figure 10:
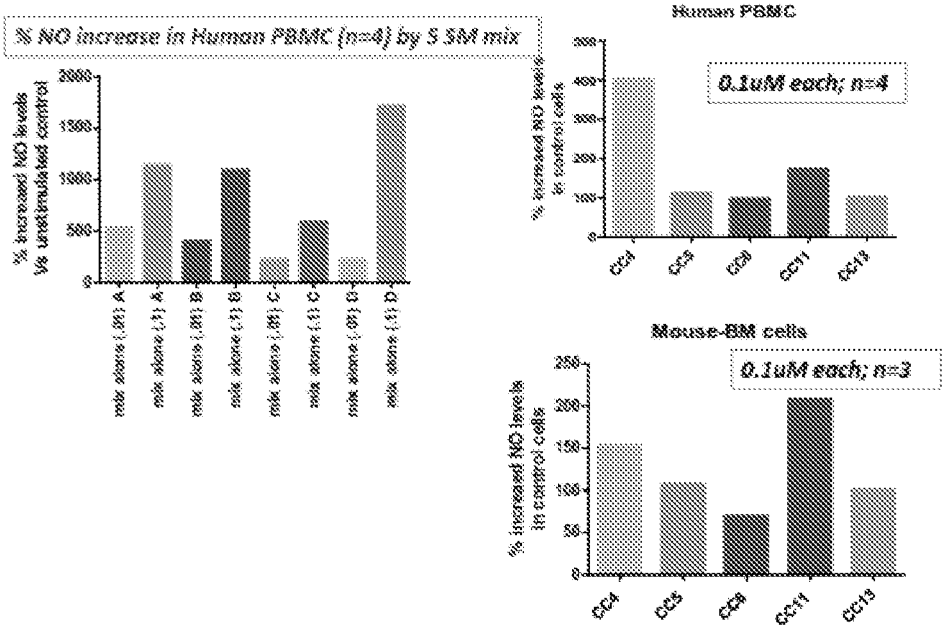
FIG. 10 depicts NOSIP antagonists SM alone or in combination increases NO levels in human PBMCs via calorimetry for nitrite concentration using Griess reagent.

NOSIP Antagonists SM Alone or in Combination Increases NO Levels in Human PBMCs:

PBMCs (1 million cells/ml) from healthy individuals' blood was isolated and were treated with or without NOSIP antagonists (either alone or mixture of equimolar concentration of all 5 small molecule antagonists at 0.1 and 0.01 μM) for 30 min in triplicate wells and incubated for 24 h at 37 °C. The culture supernatants were analysed by calorimetry for nitrite concentration using Griess reagent, and the NO levels are shown as mean percent increase over untreated control. Results are shown in FIG. 10. The panel on the right top of FIG. 10 depict nitrite levels by individual small molecules in human PBMCs. A comparison of quantities of nitric oxide produced by individual small molecules and equimolar mixture of all 5 small molecules reveals clear synergistic effect of the mixture in inducing nitric oxide. This also suggests the need for using the mixture to induce biologically effective increase in nitric oxide. Mouse BMDMs and the panel on the right bottom of FIG. 10 shows levels of nitric oxide production by individual small molecules by BMDM of mouse. A closer analysis of panels in right bottom and right top indicates that human and mouse cells respond differently to individual small molecules. For e.g. CC4 is more effective than molecules in human cells and CC11 is more effective with mouse cells—BMDM. Thus a combined mixture of 5 small molecules will be desirable for use in mouse as well as humans.

Example 10

Figure 11:
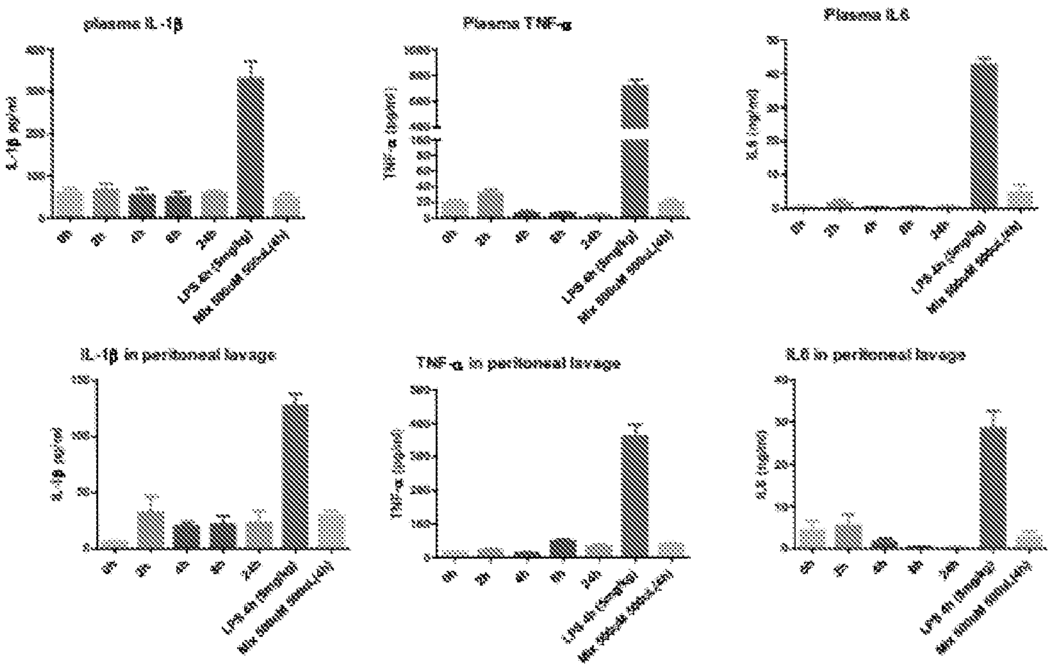
FIG. 11 illustrates intraperitoneal administration of NOSIP Antagonists to mice does not significantly increase inflammatory cytokines in peritoneal fluid and plasma unlike positive control LPS.

Induction of NO Production by NOSIP Antagonist Cocktail is not Associated with Induction of Inflammatory Cytokines:

A mixture of all 5 Small molecule 'NOISP antagonists' were injected by intra-peritoneal route (100 μl/mouse of 100 μM) and groups of mice were sacrificed at different time points and plasma and peritoneal lavage were harvested and inflammatory cytokines (IL-1β, TNF-α and IL-6) levels were quantified using ELISA kits. Administration of NOSIP antagonist SM did not induce the inflammatory cytokines in plasma and in Peritoneal fluid. LPS (5 mg/kg) was used as a positive control. Higher dose of NOSIP antagonists SM cocktail (500 μl of 500 μM, i.p.) also did not influence inflammatory cytokine production in vivo. The results are shown in FIG. 11.

Example 11

SM NOSIP Antagonists Induce Type 1 Interferons in a Murine Macrophage Cell Line RAW—IFNa5 and IFNa6 and IFN-b are Significantly Raised in Treated Macrophages:

The murine macrophage cell line, RAW 264.7 (ATCC® TIB-71™) was maintained in RPMI-1640 medium (PAN Biotech, Aidenbach Germany) supplemented with antibiotics, including penicillin (100 U/ml) and streptomycin (0.1 mg/ml), 2.0 mM L-glutamine (Himedia Laboratories Pvt. Ltd., Mumbai, India), and 10% heat-inactivated FBS (PAN Biotech, Aidenbach Germany) at 37 °C in a humidified incubator with 5% CO2. 8-12 week old male mice was sacrificed via cervical dislocation and legs were dissected. Bone marrow from tibia and femur bones was flushed out using a 25-gauge needle and a 10 ml syringe filled with DMEM (HiMedia Laboratory, Mumbai, India) containing 10% FBS (Gibco Laboratories, USA) under aseptic condition. The cell suspension was centrifuged at 2000 r.p.m for 5 min at room temperature to pellet cells. The supernatant was discarded and cells were resuspended in DMEM containing 10% FBS.

Quantitative Real-Time PCR (qRT-PCR) Analysis

For qRT-PCR analysis, RAW 264.7 cells were cultured in 6 well plate at $2\times10^6$ cells/2 ml in RPMI 1640 containing 10% FBS and incubated overnight at 37 °C and 5% $CO_2$ in a humidified incubator. Next day, the cells were washed with RPMI 1640 media and either treated or untreated with different concentrations of SM (5 μM or 15 μM). The BMDM cell suspension was cultured in 24 well plate at $5\times10^6$ cells/1.5 ml in DMEM supplemented with 10% FBS, 1% antibiotic-antimycotic solution (Gibco Laboratories, USA). The cells were incubated overnight at 37 °C and 5% $CO_2$ in a humidified incubator. Next day, the culture wells were gently washed 2 times with 1 ml with DMEM medium to remove non-adherent cells. The cells were either treated or untreated with LPS (1 μg/ml) or SM (5 μM or 15 μM). After 8 h, BMDM and RAW 264.7 cells were lysed in 1 ml TRIzol reagent (Thermo Fisher Scientific, IL, USA). Total RNA was extracted with molecular grade reagents according to the instructions provided by the manufacturer (Sigma; St. Louis, MO, USA). First-strand cDNA synthesis was carried out with 0.5 μg of total RNA using random primers and high capacity cDNA reverse transcription kit (Thermo Fisher Scientific, IL, USA). Real-time quantitative PCR was performed using SYBR select master mix (Thermo Fisher Scientific, IL, USA). At the end of PCR, dissociation curve analysis was performed to verify the amplification of a single product. Relative expression of inflammatory cytokines and interferon subtypes were calculated using $2^{-\Delta\Delta CT}$ method [Pfaffl, Michael W. "A new mathematical model for relative quantification in real-time RT-PCR." Nucleic acids research 29, no. 9 (2001): e45-e45.].

Sequence of the Primers Used for qPCR

The forward and reverse primers of genes used were:

IL-1: Forward primer: SEQ ID No: 1; Reverse primer: SEQ ID No: 2

IL-6: Forward primer: SEQ ID No: 3; Reverse primer: SEQ ID No: 4

IL-10: Forward primer: SEQ ID No: 5; Reverse primer: SEQ ID No: 6

TNF α: Forward primer: SEQ ID No: 7; Reverse primer: SEQ ID No: 8

IFN α1: 5 Forward primer: SEQ ID No: 9; Reverse primer: SEQ ID No: 10

IFN α2: Forward primer: SEQ ID No: 11; Reverse primer: SEQ ID No: 12

IFN α5: Forward primer: SEQ ID No: 13; Reverse primer: SEQ ID No: 14

IFN α6: Forward primer: SEQ ID No: 15; Reverse primer: SEQ ID No: 16

IFN α7: Forward primer: SEQ ID No: 17; Reverse primer: SEQ ID No: 18

IFN β: Forward primer: SEQ ID No: 19; Reverse primer: SEQ ID No: 20

β-actin: Forward primer: SEQ ID No: 21; Reverse primer: SEQ ID No: 22

Figure 12:
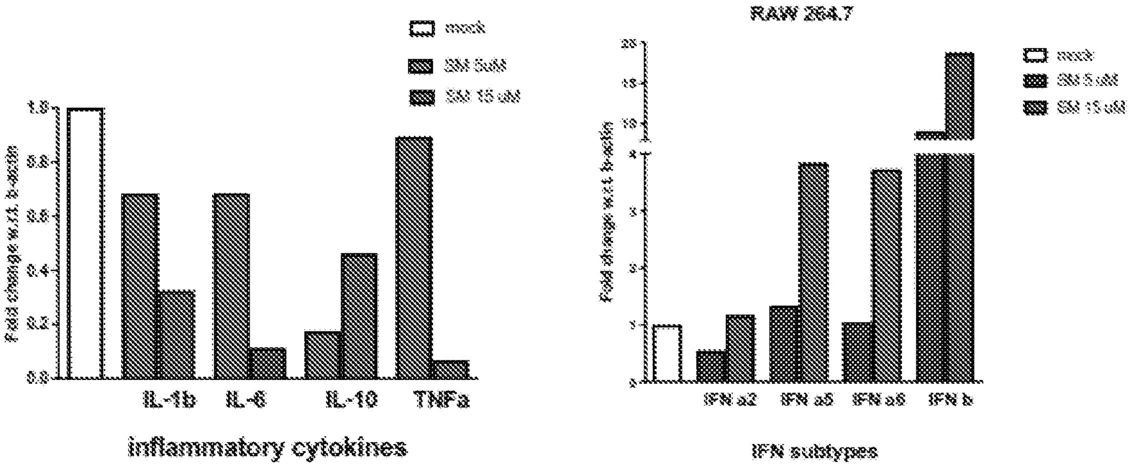
FIG. 12 is a graphical representation of Q-RT PCR results for cytokine genes (12a) and Type 1 Interferon genes (12 b) in RAW 264.7 cells treated with SM NOSIP antagonists for 10 hours.

Significant induction of type 1 Interferons and absence of induction of inflammatory cytokines (TNF-α, IL-b and IL-6) were quantified by Q-RT-PCR and the results are shown in FIG. 12. The right panel shows of over expression of Type 1 IFN genes by SM NOSIP Antagonists and the panel on the left reveals very low induction of inflammatory cytokines.

Example 11

Figure 13:
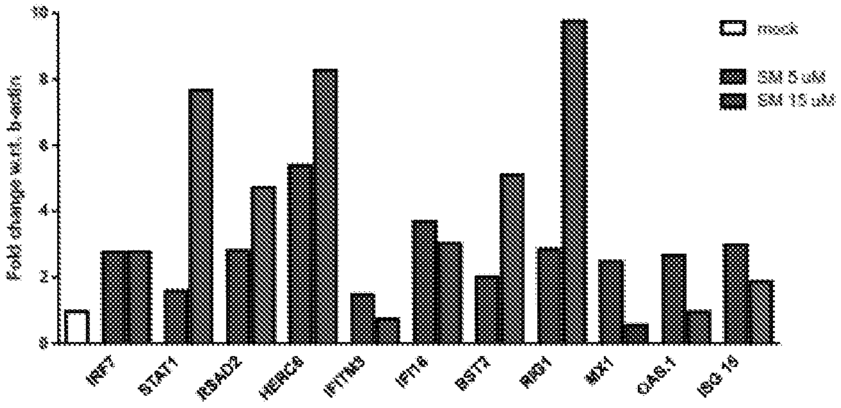
FIG. 13 is a graphical representation of Q-RT PCR results for Interferon stimulated genes in RAW 264.7 cells treated with SM NOSIP antagonists for 10 hours.

SM NOSIP Antagonists Induce Several Interferon Stimulated Genes when Murine Macrophage Cell Lines RAW were Treated In Vitro for 8 Hrs:

RAW 264.7 were treated with different concentration of SM (5 μM or 15 μM). After 8 h of treatment, RNA was isolated, reverse transcribed to cDNA which was quantified by qRT-PCR. Values were normalized to R-actin mRNA content, and control cells were assigned a value of 1. Relative expression was calculated using the $2^{-\Delta\Delta CT}$ method. Values are expressed as Mean±SEM. Details of genes overexpressed by SM NOSIP antagonists are shown in FIG. 13.

Example 12

Figure 14:
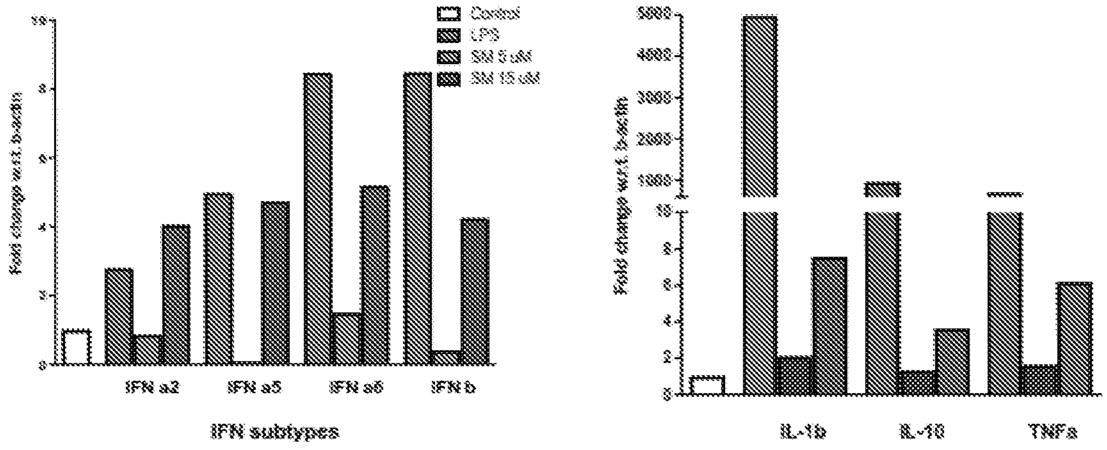
FIG. 14 is a graphical representation of Q-RT PCR for Type 1 Interferon genes (FIG. 14 (*a*) on the left) and cytokine genes (FIG. 14 (*b*) on the right) in murine BMDM cells treated with SM NOSIP antagonists for 8 hours.

Q-RT PCR for Type 1 Interferon genes (14 a) and cytokine genes (14 b) in murine BMDM cells treated with SM NOSIP antagonists for 8 hrs: BMDM were treated with LPS (1 μg/ml) and different concentration of SM (5 μM or 15 μM). After 8 h of treatment, RNA was isolated, reverse transcribed to cDNA which was quantified by qRT-PCR. Values were normalized to R-actin mRNA content, and control cells were assigned a value of 1. Relative expression was calculated using the $2^{-\Delta\Delta CT}$ method. Values are expressed as Mean±SEM. Details of the results are shown in FIG. 14. The left panel shows of inflammatory over expression of Type 1 IFN genes by SM NOSIP Antagonists comparable to LPS and the panel on the right reveals very low induction of inflammatory cytokines unlike the positive control LPS that induced very high induction of inflammatory cytokines. The results are shown in FIG. 14.

Source and geographical origin of the biological materials and reagents used:

TABLE 4

| SN | Chemicals/Reagents | Supplier details | Catalogue. Number |
|---|---|---|---|
| 1 | Ni-NTA agarose | Qiagen, Germantown, MD 20874, USA. | 30210 |
| 2 | DAF FM Diacetate | Thermo Fisher Scientific, Waltham, MA, USA | D23842 |
| 3 | Protease Inhibitor cocktail | Sigma, Saint Louis, Missouri, USA. | P8465 |
| 4 | Isopropyl ß-D-1-thiogalactopyranoside, Isopropyl ß-D-thiogalactoside (IPTG) | Sigma, St. Louis, MO, USA. | I6758 |
| 5 | Ampicillin sodium salt | Sigma, St. Louis, MO, USA. | A0166 |
| 6 | Polyvinylidene difluoride (PVDF) membrane | Sigma, St. Louis, MO, USA. | Z613835 |
| 7 | Amicon Ultracel | Millipore, Darmstadt, Germany. | UFC900324 |
| 8 | Nitrite Assy Kit | Sigma, St. Louis, MO, USA. | 23479 |
| 9 | Penicillin Streptomycin 100x solution (cytiva hyclone) | Thermo Fisher Scientific, Waltham, MA, USA. | SV30010 |
| 10 | ProteOn GLC Sensor Chip | Biorad, Hercules, California, USA. | 176-5011 |
| 11 | ProteOn Amine Coupling Kit | Biorad, Hercules, California, USA. | 176-2410 |
| 12 | Bradford reagent | Sigma, St. Louis, MO, USA. | B6916 |
| 13 | Luminal reagent | Santa Cruz Biotechnology, Finnell Street Dallas, USA. | sc-2048 |
| 14 | RPMI-1640 | PAN Biotech, Aidenbach Germany | P04-17500 |
| 15 | Protein G sepharose | Sigma, St. Louis, MO, USA. | P3296 |
| 16 | L-Glutamine | Himedia Laboratories Pvt. Ltd., Mumbai, India | TC243 |

TABLE 4-continued

| SN | Chemicals/Reagents | Supplier details | Catalogue. Number |
|---|---|---|---|
| 17 | Fetal Bovine Serum. | Gibco, Thermo Fisher Scientific, Waltham, MA, USA. | 26140079 |
| 18 | Multiplex Luminex system | Millipore, MA, USA. | MCYTMAG-70K-PX32 |
| 19 | Nunc MaxiSorp flat-bottom | Thermo Fisher Scientific, Waltham, MA, USA. | 44-2404-21 |
| 20 | o-Phenylenediamine dihydrochloride (OPD) peroxidase substrate | Sigma-Aldrich, Saint Louis, Missouri, USA. | P1526 |
| 21 | Hydrogen peroxide solution | Sigma-Aldrich, Saint Louis, MO, USA. | H1009 |
| 22 | Bovine Serum Albumins | Sigma-Aldrich, Saint Louis, MO, USA. | A4612 |
| 23 | DMEM | Himedia Laboratories Pvt. Ltd., Mumbai, India | AT186 |
| 24 | Tween-20 | Sigma-Aldrich, Saint Louis, MO, USA. | P1379 |
| 25 | High Capacity Cdna Reverse Trans Kit | Thermo Fisher Scientific, Waltham, MA, USA. | 4368814 |
| 26 | Antifade Solution | Life Technologies Corporation, Willow Creek Road, Eugene. | P36982 |
| 27 | DAPI (4',6-Diamidino-2-Phenylindole, Dihydrochloride) | Invitrogen Ltd., Paisley PA4 9RF, UK. | D1306 |
| 28 | QIAamp RNA Blood Mini Kit (50) | Qiagen, Germantown, MD 20874, USA. | 52304 |
| 29 | TRIzol reagent | Thermo Fisher Scientific, Waltham, MA, USA. | 10296028 |
| 30 | PowerUp ™ SYBR ™ Green Master Mix (5 ML) | Thermo Fisher Scientific, Waltham, MA, USA. | A25742 |
| 31 | IL6 Mouse uncoated ELISA kit. | Thermo Fisher Scientific, Waltham, MA, USA. | 88-7064-22 |
| 32 | IL10 Mouse uncoated ELISA kit. | Thermo Fisher Scientific, Waltham, MA, USA. | 88-7105-22 |
| 33 | IL1b Mouse uncoated ELISA kit. | Thermo Fisher Scientific, Waltham, MA, USA. | 88-7013-22 |
| 34 | TNFa Mouse uncoated ELISA kit. | Thermo Fisher Scientific, Waltham, MA, USA. | 88-7324-22 |
| 35 | IL-1b(F & R):<br>5-TGCCACCTTTTGACAGTGATG-3<br>5-AAGGTCCACGGGAAAGACAC-3 | Eurofins scientific, Luxembourg. | |
| 36 | IL-6(F & R):<br>5-TCCAGTTGCCTTCTTGGGAC-3<br>5-GCCATTGCACAACTCTTTTCTCA-3 | Eurofins scientific, Luxembourg. | |

TABLE 4-continued

| SN | Chemicals/Reagents | Supplier details | Catalogue. Number |
|---|---|---|---|
| 37 | IL-10(F & R): 5-GGTTGCCAAGCCTTATCGGA-3; 5-AATCGATGACAGCGCCTCAG-3 | Eurofins scientific, Luxembourg. | |
| 38 | TNF α(F & R): 5-CAGAGGGAAGAGTTCCCA-3; 5-CCTTGGTCTGGTAGGAGACG-3 | Eurofins scientific, Luxembourg. | |
| 39 | IFN α1(F & R): 5-GAG AAG AAA CAC AGC CCC TG-3; 5-TCA GTC TTC CCA GCA CAT TG-3 | Eurofins scientific, Luxembourg. | |
| 40 | IFN α2(F & R): 5-GTG CAG GAA CCT CTG AC-3; 5-CTT CTG CTC TGA CCA CCT CC-3 | Eurofins scientific, Luxembourg. | |
| 41 | IFN α5(F & R): 5-GAC TCA TCT GCT GCA TGG AA-3; 5-TGT TGC ATC ACA CAG GCT TT-3 | Eurofins scientific, Luxembourg. | |
| 42 | IFN α6(F & R): 5-TCC ATC AGC AGC TCA ATG AC-3; 5-TAT GTC CTC ACA GCC AGC AG-3 | Eurofins scientific, Luxembourg. | |
| 43 | IFN α7(F & R): 5-CTG CCT GAA GGA CAG AAA GG-3; and, 5-ATG CAG AAC ACA GAG GGC TT-3 | Eurofins scientific, Luxembourg. | |
| 44 | IFN ß(F & R): 5-TCT GGA GCA TCT CTT GGA TGG CAA-3, 5-TCC AGC TCC AAG AAA GGA CGA ACA-3 | Eurofins scientific, Luxembourg. | |
| 45 | ß-actin(F & R): 5-GATTACTGCTCTGGCTCCTAGC-3; and 5-GACTCATCGTACTCCTGCTTGC-3 | Eurofins scientific, Luxembourg. | |
| 46 | SAMHD1 (F & R): 5-ATGTTTTCCCTGGAGCGTC-3, 5-GCTCACTGATCTGTAGCTCTG-3 | Eurofins scientific, Luxembourg. | |
| 47 | IRF7 (F & R): 5-TTGATCCGCATAAGGTGTACG-3, 5-TTCCCTATTTTCCGTGGCTG-3 | Eurofins scientific, Luxembourg. | |
| 48 | STAT1(F & R): 5-CCAAAGGAAGCACCAGAACC-3, 5-GGGTGGACTTCAGACACAGA-3 | Eurofins scientific, Luxembourg. | |
| 49 | RSAD (F & R): 5-GAAACATTCTTGGAGCGTCAC-3, 5-CCGGTACAGTTCAGAAAGCG-3 | Eurofins scientific, Luxembourg. | |
| 50 | ISG15 (F & R): 5-GAGAGCAAGCAGCCAGAAG-3, 5-CCCAGGCCATTGCTGCAGGC-3 | Eurofins scientific, Luxembourg. | |
| 51 | OAS.1 (F & R): 5-AGGTGGAGTTTGATGTGCTG-3, 5-GTAGAGAACTCGCCATCCTTC-3. | Eurofins scientific, Luxembourg. | |
| 52 | IFITM (F & R): 5-CCGTGAAGTCTAGGGACAGG-3, 5-GACAACGATGACGACGATGG-3 | Eurofins scientific, Luxembourg. | |
| 53 | IFI16 (F & R): 5-CATTTGTGAGTGGAGAGTACTTAGT-3, 5-CCTGACATTGGTGAGTCTTCC-3. | Eurofins scientific, Luxembourg. | |
| 54 | RIG1 (F & R): 5-CATTCTCTATGAGTACGTGGGC-3 & 5-ACTTGCTATCTCGTGCTCTTC-3. | Eurofins scientific, Luxembourg. | |

TABLE 4-continued

| SN | Chemicals/Reagents | Supplier details | Catalogue. Number |
|---|---|---|---|
| 55 | MX1 (F & R): 5-AGGCAGTGGTATTGTCACCA-3 & 5-AGACTTTGCCTCTCCACTCC-3. | Eurofins scientific, Luxembourg. | |
| 56 | BST2 (F & R): 5-GTCACTGTTCCTGCTCTTTTG-3 & 5-GGTTTCCACATCCTCAGGG-3 | Eurofins scientific, Luxembourg. | |
| 57 | The murine macrophage cells, RAW 264.7 | Procured from ATCC cell repository | |
| 58 | Murine Bone marrow derived mononuclear cells | Primary BMDM cells prepared from bone marrows dissected out from normal BALB/c mice being maintained at the animal facility of the institute. Breeding pairs of BALB/c mice were obtained from National Institute of Immunology, Delhi and bred in the animal facility of Institute of Life Sciences | |
| 59 | Male C57BL/6 mice | Breeding pairs of C57BL/6 mice were obtained from National Institute of Immunology, Delhi and bred in the animal facility of Institute of Life Sciences | |
| 60 | Human PBMC | PBMCs were prepared from peripheral blood collected from normal human volunteers after taking due consent | |

The animal and cells disclosed in the examples of the present invention were procured solely for the purpose of research and experimentation to generate additional data. The invention is based on a composition and do not claim or intend to commercialize any biological material.

We claim:

1. A pharmaceutical composition for enhancing intracellular nitric oxide in a subject, the said composition comprising:

(i) 1-{3-[9-methoxy-7-(2-methoxyphenyl)-2,3,4,5-tetrahydro-1,4-benzoxazepine-4-carbonyl] phenyl}imidazolidin-2-one, (ii) N-tert-butyl-2-{N-[(furan-2-yl) methyl]-2-[5-(4-methylphenyl)-2H-1,2,3,4-tetrazol-2-yl]acetamido}-2-(4-hydroxyphenyl) acetamide (iii) 3-[2-(2-{[(6-hydroxy-2,4-dioxo-1,2,3,4-tetrahydropyrimidin-5-yl)(4hydroxyphenyl) methyl]amino}-4-oxo-4,5-dihydro-1,3-thiazol-5-yl)acetamido]benzoic acid (iv) 2-oxo-2-(1H-pyrrol-2-yl)ethyl 2-[(4-fluorophenyl) methoxy]benzoate, and (v) 5-(3-{[(3-bromo-4-hydroxy-5 methoxyphenyl) methylidene]amino}-2(butylimino)-2,3-dihydro-1,3-thiazol-4-yl)-2-hydroxybenzamide.

2. The composition, as claimed in claim 1, wherein the components are present in an equimolar concentration in phosphate buffer saline.

3. The composition as claimed in claim 1, wherein the components inhibit nitric oxide snynthase interacting proteins and inducible Nitric oxide synthase interaction.

4. The composition as claimed in claim 1, wherein the components are small molecule, Nitric oxide synthase interacting proteins antagonists, with molecular weight in the range of 382-682u.

5. The composition as claimed in claim 1, wherein the components either standalone or in combination enhances nitric oxide level at 0.1 and 0.01 μM concentrations of the composition.

6. The composition as claimed in claim 1, wherein the increase in nitric oxide level in vitro is measured via increase in nitrite levels in the cell culture supernatant.

* * * * *

SEQUENCE LISTING

<160> NUMBER OF SEQ ID NOS: 28

<210> SEQ ID NO 1
<211> LENGTH: 21
<212> TYPE: DNA
<213> ORGANISM: Human

<400> SEQUENCE: 1
tgccaccttt tgacagtgat g 21

<210> SEQ ID NO 2
<211> LENGTH: 20
<212> TYPE: DNA
<213> ORGANISM: Human

<400> SEQUENCE: 2

-continued aaggtccacg ggaaagacac 20

<210> SEQ ID NO 3
<211> LENGTH: 20
<212> TYPE: DNA
<213> ORGANISM: Human

<400> SEQUENCE: 3
tccagttgcc ttcttgggac 20

<210> SEQ ID NO 4
<211> LENGTH: 23
<212> TYPE: DNA
<213> ORGANISM: Human

<400> SEQUENCE: 4
gccattgcac aactcttttc tca 23

<210> SEQ ID NO 5
<211> LENGTH: 20
<212> TYPE: DNA
<213> ORGANISM: Human

<400> SEQUENCE: 5
ggttgccaag ccttatcgga 20

<210> SEQ ID NO 6
<211> LENGTH: 20
<212> TYPE: DNA
<213> ORGANISM: Human

<400> SEQUENCE: 6
aatcgatgac agcgcctcag 20

<210> SEQ ID NO 7
<211> LENGTH: 18
<212> TYPE: DNA
<213> ORGANISM: Human

<400> SEQUENCE: 7
cagagggaag agttccca 18

<210> SEQ ID NO 8
<211> LENGTH: 20
<212> TYPE: DNA
<213> ORGANISM: Human

<400> SEQUENCE: 8
ccttggtctg gtaggagacg 20

<210> SEQ ID NO 9
<211> LENGTH: 20
<212> TYPE: DNA
<213> ORGANISM: Human

<400> SEQUENCE: 9
gagaagaaac acagcccctg 20

<210> SEQ ID NO 10
<211> LENGTH: 20
<212> TYPE: DNA
<213> ORGANISM: Human

-continued

<400> SEQUENCE: 10
tcagtcttcc cagcacattg 20

<210> SEQ ID NO 11
<211> LENGTH: 17
<212> TYPE: DNA
<213> ORGANISM: Human

<400> SEQUENCE: 11
gtgcaggaac ctctgac 17

<210> SEQ ID NO 12
<211> LENGTH: 20
<212> TYPE: DNA
<213> ORGANISM: Human

<400> SEQUENCE: 12
cttctgctct gaccacctcc 20

<210> SEQ ID NO 13
<211> LENGTH: 20
<212> TYPE: DNA
<213> ORGANISM: Human

<400> SEQUENCE: 13
gactcatctg ctgcatggaa 20

<210> SEQ ID NO 14
<211> LENGTH: 20
<212> TYPE: DNA
<213> ORGANISM: Human

<400> SEQUENCE: 14
tgttgcatca cacaggcttt 20

<210> SEQ ID NO 15
<211> LENGTH: 20
<212> TYPE: DNA
<213> ORGANISM: Human

<400> SEQUENCE: 15
tccatcagca gctcaatgac 20

<210> SEQ ID NO 16
<211> LENGTH: 20
<212> TYPE: DNA
<213> ORGANISM: Human

<400> SEQUENCE: 16
tatgtcctca cagccagcag 20

<210> SEQ ID NO 17
<211> LENGTH: 20
<212> TYPE: DNA
<213> ORGANISM: Human

<400> SEQUENCE: 17
ctgcctgaag gacagaaagg 20

<210> SEQ ID NO 18
<211> LENGTH: 20
<212> TYPE: DNA
<213> ORGANISM: Human

<400> SEQUENCE: 18
atgcagaaca cagagggctt 20

<210> SEQ ID NO 19
<211> LENGTH: 24
<212> TYPE: DNA
<213> ORGANISM: Human

<400> SEQUENCE: 19
tctggagcat ctcttggatg gcaa 24

<210> SEQ ID NO 20
<211> LENGTH: 24
<212> TYPE: DNA
<213> ORGANISM: Human

<400> SEQUENCE: 20
tccagctcca agaaaggacg aaca 24

<210> SEQ ID NO 21
<211> LENGTH: 22
<212> TYPE: DNA
<213> ORGANISM: Human

<400> SEQUENCE: 21
gattactgct ctggctccta gc 22

<210> SEQ ID NO 22
<211> LENGTH: 22
<212> TYPE: DNA
<213> ORGANISM: Human

<400> SEQUENCE: 22
gactcatcgt actcctgctt gc 22

<210> SEQ ID NO 23
<211> LENGTH: 912
<212> TYPE: DNA
<213> ORGANISM: Human

<400> SEQUENCE: 23
catatgacgc gccacggcaa aaattgcacg gcgggtgcgg tttataccta ccacgaaaaa 60
aaaaaagaca cggcagcaag cggctacggc acccaaaaca ttcgtctgag ccgcgatgca 120
gtgaaagatt ttgactgctg ttgcctgagc ctgcaaccgt gccatgatcc ggtggttacg 180
ccggacggct atctgtacga acgtgaagct attctggaat atatcctgca tcagaaaaaa 240
gaaattgcgc gtcaaatgaa agcctacgaa aaacagcgcg gcacccgtcg cgaagaacag 300
aaagaactgc aacgtgcggc cagccaagat catgtccgcg gttttctgga aaaagaaagc 360
gccatcgtgt ctcgcccgct gaatccgttc accgcaaaag ctctgagcgg tacgagcccg 420
gatgatgttc agccgggtcc gagcgtcggt ccgccgagca aagataaaga caaagtgctg 480
ccgagctttt ggattccgag cctgaccccg gaagcgaaag ccacgaaact ggaaaaaccg 540
agccgtaccg tgacgtgccc gatgagcggc aaaccgctgc gcatgtctga tctgaccccg 600
gttcacttca cgccgctgga tagctctgtt gaccgtgtcg gtctgattac ccgtagcgaa 660
cgctatgtgt gcgcggttac ccgtgacagc ctgagcaatg caacgccgtg cgctgttctg 720
cgcccgtctg gtgcggttgt gaccctggaa tgcgtcgaaa aactgatccg taaagatatg 780
gttgatccgg tgaccggcga taaactgacg gatcgtgaca ttatcgttct gcaacgtggc 840
ggcaccggtt tcgcaggcag cggtgtgaaa ctgcaagctg aaaaaagccg cccggttatg 900
caggcgctcg ag 912

<210> SEQ ID NO 24
<211> LENGTH: 1284
<212> TYPE: DNA
<213> ORGANISM: Human

<400> SEQUENCE: 24
catatgccgc gccatgttcg tatcaaaaat tggggtagcg gtatgacgtt tcaggatacg 60
ctgcatcata aagcaaaagg catcctgacc tgccgtagca aatcttgcct gggtagcatc 120
atgaccccga aaagcctgac gcgtggcccg cgcgataaac cgaccccgcc ggatgaactg 180
ctgccgcagg cgatcgaatt tgtgaaccag tactacggta gcttcaaaga agccaaaatt 240
gaagaacatc tggcgcgcgt tgaagccgtc accaaagaaa tcgaaaccac gggcacctac 300
cagctgacgg gcgatgaact gatttttgca acgaaacagg cgtggcgtaa cgcgccgcgt 360
tgcattggcc gtatccagtg gagcaatctg caggtctttg atgcccgcag ctgcagcacc 420
gcacgtgaaa tgttcgaaca tatctgccgt catgttcgct atagcaccaa caatggtaac 480
attcgtagcg cgatcacggt gtttccgcag cgcagcgatg gcaaacatga tttccgtgtt 540
tggaatgcac agctgattcg ctacgcgggt tatcagatgc cggatggcag catccgcggt 600
gatccggcaa acgtggaatt tacccagctg tgcatcgatc tgggttggaa accgaaatat 660
ggccgtttcg atgtggttcc gctggttctg caggccaatg gccgcgatcc ggaactgttt 720
gaaattccgc cggatctggt gctggaagtt gcaatggaac atccgaaata cgaatggttc 780
cgtgaactgg aactgaaatg gtatgcactg ccggcagttg caaacatgct gctggaagtc 840
ggcggtctgg aatttccggg ttgcccgttc aatggctggt acatgggcac cgaaattggc 900
gtccgcgatt tttgcgatgt gcagcgttat aacatcctgg aagaagtggg tcgtcgcatg 960
ggcctggaaa cgcataaact ggccagcctg tggaaagatc aggcagtcgt ggaaattaac 1020
atcgcagtcc tgcattcttt tcagaaacag aatgtgacca ttatggatca tcatagcgcg 1080
gccgaatctt tcatgaaata catgcagaac gaatatcgtt ctcgcggcgg ttgcccggcg 1140
gattggattt ggctggttcc gccgatgagc ggcagcatca ccccggtttt tcatcaggaa 1200
atgctgaact atgtcctgag cccgttctat tactatcagg tggaagcctg gaaaacgcat 1260
gtttggcagg atgaaaaact cgag 1284

<210> SEQ ID NO 25
<211> LENGTH: 14
<212> TYPE: PRT
<213> ORGANISM: Human

<400> SEQUENCE: 25

Thr Gly Asp Glu Leu Ile Phe Ala Thr Lys Gln Ala Trp Arg
1               5                   10

<210> SEQ ID NO 26
<211> LENGTH: 18
<212> TYPE: PRT
<213> ORGANISM: Human

<400> SEQUENCE: 26

Asn Gln Tyr Tyr Gly Ser Phe Lys Glu Ala Lys Ile Glu Glu His Leu
1               5                   10                  15

-continued

```
Ala Arg


<210> SEQ ID NO 27
<211> LENGTH: 34
<212> TYPE: PRT
<213> ORGANISM: Human

<400> SEQUENCE: 27

Gly Trp Lys Pro Lys Tyr Gly Arg Phe Asp Val Val Pro Leu Val Leu
1               5                   10                  15

Gln Ala Asn Gly Arg Asp Pro Glu Leu Phe Glu Ile Pro Pro Asp Leu
            20                  25                  30

Val Leu


<210> SEQ ID NO 28
<211> LENGTH: 33
<212> TYPE: PRT
<213> ORGANISM: Human

<400> SEQUENCE: 28

Asn Leu Gln Val Phe Asp Ala Arg Ser Cys Ser Thr Ala Arg Glu Met
1               5                   10                  15

Phe Glu His Ile Cys Arg His Val Arg Tyr Ser Thr Asn Asn Gly Asn
            20                  25                  30

Ile
```